United States Patent
Crook et al.

(10) Patent No.: US 11,272,924 B2
(45) Date of Patent: Mar. 15, 2022

(54) KNOTLESS CLOSURE SUTURES AND METHODS OF TISSUE FIXATION

(71) Applicant: Arthrex, Inc., Naples, FL (US)

(72) Inventors: Loren D. Crook, Estero, FL (US); Peter J. Dreyfuss, Naples, FL (US); Amr W. Elmaraghy, Mississuaga (CA)

(73) Assignee: ARTHREX, INC., Naples, FL (US)

(*) Notice: Subject to any disclaimer, the term of this patent is extended or adjusted under 35 U.S.C. 154(b) by 572 days.

(21) Appl. No.: 16/038,900

(22) Filed: Jul. 18, 2018

(65) Prior Publication Data

US 2020/0022701 A1    Jan. 23, 2020

(51) Int. Cl.
| | |
|---|---|
| *A61B 17/06* | (2006.01) |
| *A61B 17/04* | (2006.01) |
| *A61B 17/00* | (2006.01) |

(52) U.S. Cl.
CPC .... *A61B 17/06166* (2013.01); *A61B 17/0491* (2013.01); *A61B 2017/00867* (2013.01); *A61B 2017/045* (2013.01); *A61B 2017/0456* (2013.01); *A61B 2017/06176* (2013.01); *A61B 2017/06185* (2013.01)

(58) Field of Classification Search
CPC .... A61B 17/06166; A61B 2017/06176; A61B 2017/06185; A61B 2017/0412; A61B 2017/0461; A61B 2017/0458
See application file for complete search history.

(56) References Cited

U.S. PATENT DOCUMENTS

| | | |
|---|---|---|
| 3,130,728 A | 4/1964 | Pearson et al. |
| 3,942,532 A | 3/1976 | Hunter et al. |
| 4,510,934 A | 4/1985 | Batra |
| 4,640,178 A | 2/1987 | Kurzbock |
| 4,662,886 A | 5/1987 | Moorse et al. |
| 4,946,467 A | 8/1990 | Ohi et al. |
| 4,950,285 A | 8/1990 | Wilk |
| 5,128,197 A | 7/1992 | Kobayashi et al. |
| 5,178,629 A * | 1/1993 | Kammerer ......... A61B 17/0469 606/148 |
| 5,370,661 A | 12/1994 | Branch |
| 5,593,424 A | 1/1997 | Northrup I |
| 5,667,528 A | 9/1997 | Colligan |

(Continued)

FOREIGN PATENT DOCUMENTS

| | | |
|---|---|---|
| EP | 0476306 A2 | 3/1992 |
| EP | 2501300 B1 | 7/2018 |

OTHER PUBLICATIONS dictionary.com, definition of "taper", 2016. https://www.dictionary.com/browse/taper?s=t (Year: 2016).*

(Continued)

*Primary Examiner* — Todd J Scherbel
*Assistant Examiner* — Mikail A Mannan
(74) *Attorney, Agent, or Firm* — Potomac Law Group PLLC

(57) ABSTRACT

Surgical suturing constructs, suture anchor assemblies, and methods of tissue fixation are disclosed. The suturing construct includes a bumpy suture. A suturing construct may include one or more small loops on a distal end. A suturing construct may include a splice terminating into a tapered portion/region at a proximal end. A bumpy suture of a suturing construct may form a knotless, closed, self-locking loop around tissue.

21 Claims, 16 Drawing Sheets

(56) References Cited

U.S. PATENT DOCUMENTS

| | | |
|---|---|---|
| 5,683,417 A | 11/1997 | Cooper |
| 5,931,855 A | 8/1999 | Buncke |
| 5,964,783 A | 10/1999 | Grafton et al. |
| 5,989,252 A | 11/1999 | Fumex |
| 6,027,523 A | 2/2000 | Schmieding |
| 6,045,574 A | 4/2000 | Thal |
| 6,143,017 A | 11/2000 | Thal |
| 6,203,564 B1 | 3/2001 | Hutton et al. |
| 6,296,659 B1 | 10/2001 | Foerster |
| 6,475,229 B1 | 11/2002 | Pagedas |
| 6,511,498 B1 | 1/2003 | Fumex |
| 6,645,226 B1 | 11/2003 | Jacobs et al. |
| 7,285,124 B2 | 10/2007 | Foerster |
| 7,329,272 B2 | 2/2008 | Burkhart et al. |
| 7,410,460 B2 | 8/2008 | Benderev |
| 7,442,202 B2 | 10/2008 | Dreyfuss |
| 7,468,068 B2 | 12/2008 | Kolster |
| 7,749,250 B2 | 7/2010 | Stone et al. |
| 7,850,894 B2 | 12/2010 | Lindh et al. |
| 7,857,830 B2 | 12/2010 | Stone et al. |
| 7,892,256 B2 | 2/2011 | Grafton et al. |
| 7,905,903 B2 | 3/2011 | Stone et al. |
| 7,959,650 B2 | 6/2011 | Kaiser et al. |
| 8,088,130 B2 | 1/2012 | Kaiser et al. |
| 8,118,834 B1 | 2/2012 | Goraltchouk et al. |
| 8,118,836 B2 | 2/2012 | Denham et al. |
| 8,137,381 B2 | 3/2012 | Foerster et al. |
| 8,161,618 B2 | 4/2012 | Maiorino et al. |
| 8,210,085 B2 | 7/2012 | Lindh et al. |
| 8,231,654 B2 | 7/2012 | Kaiser et al. |
| 8,267,961 B2 | 9/2012 | Popadiuk et al. |
| 8,273,105 B2 | 9/2012 | Cohen et al. |
| 8,273,106 B2 | 9/2012 | Stone et al. |
| 8,298,262 B2 | 10/2012 | Stone et al. |
| 8,361,113 B2 | 1/2013 | Stone et al. |
| 8,414,612 B2 | 4/2013 | Kirsch et al. |
| 8,443,506 B2 | 5/2013 | Maiorino et al. |
| 8,454,653 B2 | 6/2013 | Hadba et al. |
| 8,496,465 B2 | 7/2013 | Lauria |
| 8,545,535 B2 | 10/2013 | Hirotsuka et al. |
| 8,562,644 B2 | 10/2013 | Yuan et al. |
| 8,562,645 B2 | 10/2013 | Stone et al. |
| 8,562,647 B2 | 10/2013 | Kaiser et al. |
| 8,640,331 B2 | 2/2014 | Marczyk et al. |
| 8,641,732 B1 | 2/2014 | Goraltchouk et al. |
| 8,649,881 B2 | 2/2014 | Helgesson |
| 8,652,172 B2 | 2/2014 | Denham et al. |
| 8,663,277 B2 | 3/2014 | Collier et al. |
| 8,715,320 B2 | 5/2014 | Lindh |
| 8,721,664 B2 | 5/2014 | Ruff et al. |
| 8,721,681 B2 | 5/2014 | Ruff et al. |
| 8,733,223 B2 | 5/2014 | Lindh et al. |
| 8,795,334 B2 | 8/2014 | Astorino et al. |
| 8,821,543 B2 | 9/2014 | Hernandez et al. |
| 8,834,521 B2 | 9/2014 | Pinto et al. |
| 8,876,900 B2 | 11/2014 | Guederian et al. |
| 8,888,810 B2 | 11/2014 | Hadba et al. |
| 8,932,327 B2 | 1/2015 | Kosa et al. |
| 9,011,487 B2 | 4/2015 | Lindh, Sr. et al. |
| 9,044,224 B2 | 6/2015 | Lauria |
| 9,179,950 B2 | 11/2015 | Zajac et al. |
| 9,206,535 B2 | 12/2015 | Lindh et al. |
| 9,301,745 B2 | 4/2016 | Dreyfuss |
| 9,332,979 B2 | 5/2016 | Sullivan et al. |
| 9,345,567 B2 | 5/2016 | Sengun |
| 9,357,992 B2 | 6/2016 | Stone et al. |
| 9,463,011 B2 | 10/2016 | Dreyfuss et al. |
| 9,527,221 B2 | 12/2016 | Maiorino et al. |
| 9,539,000 B2 | 1/2017 | Hendricksen et al. |
| 9,539,004 B2 | 1/2017 | McClellan et al. |
| 2003/0050666 A1 | 3/2003 | Grafton |
| 2003/0149447 A1 | 8/2003 | Morency et al. |
| 2004/0060410 A1 | 4/2004 | Leung et al. |
| 2004/0088003 A1 | 5/2004 | Leung et al. |
| 2004/0138683 A1 | 7/2004 | Shelton et al. |
| 2004/0237736 A1 | 12/2004 | Genova et al. |
| 2005/0267531 A1 | 12/2005 | Ruff et al. |
| 2006/0079935 A1 | 4/2006 | Kolster |
| 2007/0005068 A1 | 1/2007 | Sklar |
| 2007/0038249 A1 | 2/2007 | Kolster |
| 2007/0065663 A1 | 3/2007 | Trull et al. |
| 2007/0219587 A1 | 9/2007 | Accardo |
| 2008/0065203 A1 | 3/2008 | Khalapyan |
| 2008/0132943 A1 | 6/2008 | Maiorino et al. |
| 2008/0255613 A1 | 10/2008 | Kaiser et al. |
| 2008/0281338 A1 | 11/2008 | Wohlert et al. |
| 2008/0312689 A1 | 12/2008 | Denham et al. |
| 2009/0012560 A1 | 1/2009 | Hunter et al. |
| 2009/0082805 A1* | 3/2009 | Kaiser ............... A61B 17/06166 606/228 |
| 2009/0105753 A1* | 4/2009 | Greenhalgh ......... A61L 17/145 606/228 |
| 2009/0248062 A1 | 10/2009 | Benigna |
| 2009/0306711 A1 | 12/2009 | Stone et al. |
| 2010/0298871 A1 | 11/2010 | Ruff et al. |
| 2010/0298872 A1 | 11/2010 | Berndt et al. |
| 2010/0313729 A1 | 12/2010 | Genova et al. |
| 2011/0071548 A1* | 3/2011 | Yeh ................. A61B 17/06166 606/144 |
| 2011/0213416 A1 | 9/2011 | Kaiser |
| 2011/0282386 A1 | 11/2011 | Friedrich et al. |
| 2012/0232655 A1 | 9/2012 | Lorrison et al. |
| 2012/0276232 A1 | 11/2012 | Marczyk et al. |
| 2013/0072971 A1 | 3/2013 | Kim et al. |
| 2013/0085528 A1 | 4/2013 | Dimatteo et al. |
| 2013/0226234 A1 | 8/2013 | Avelar et al. |
| 2014/0121700 A1 | 5/2014 | Dreyfuss et al. |
| 2014/0224095 A1 | 8/2014 | Maiorino et al. |
| 2014/0257384 A1 | 9/2014 | Dreyfuss et al. |
| 2015/0025552 A1 | 1/2015 | Stoll |
| 2015/0032155 A1* | 1/2015 | Dreyfuss ............... A61L 17/145 606/229 |
| 2015/0032157 A1 | 1/2015 | Dooney et al. |
| 2015/0040534 A1 | 2/2015 | Hadba et al. |
| 2015/0066079 A1 | 3/2015 | Schmieding |
| 2015/0157308 A1 | 6/2015 | Sengun |
| 2016/0270903 A1* | 9/2016 | Dreyfuss ............ A61B 17/7001 |
| 2017/0020655 A1* | 1/2017 | Dreyfuss ............ A61B 17/0401 |
| 2017/0049434 A1 | 2/2017 | Dooney et al. |
| 2017/0325802 A1 | 11/2017 | Bennett et al. |

OTHER PUBLICATIONS

Merriam-Webster Dictionary. Definition of "suture". 2006. https://www.merriam-webster.com/dictionary/suture.*
International Search Report dated Sep. 27, 2019, in International Application No. PCT/US2019/042375.

* cited by examiner

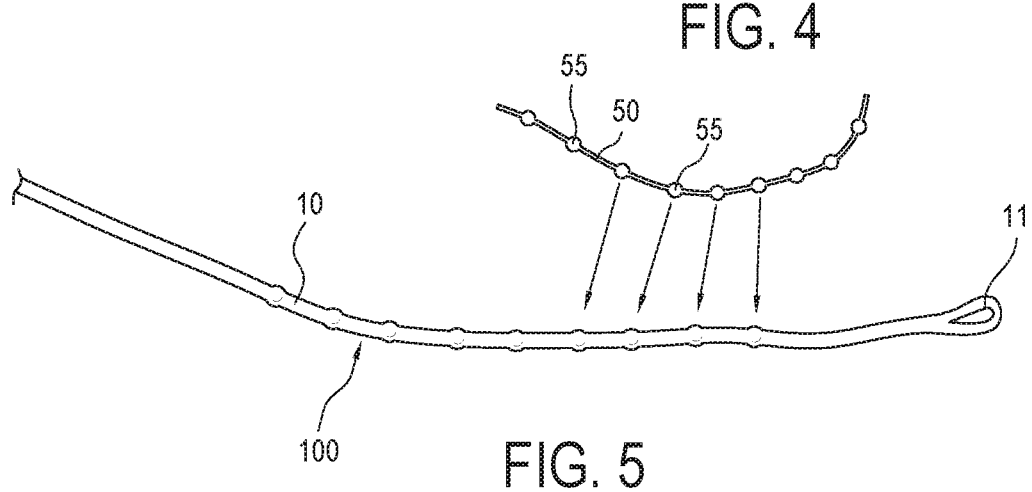
FIG. 4
FIG. 5
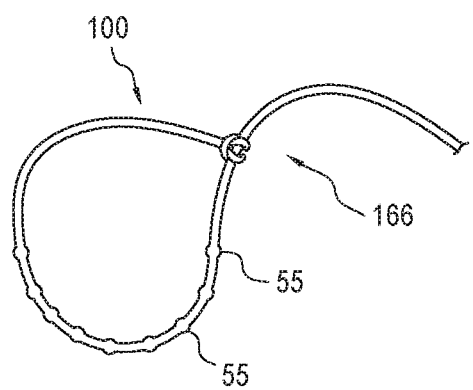
FIG. 6
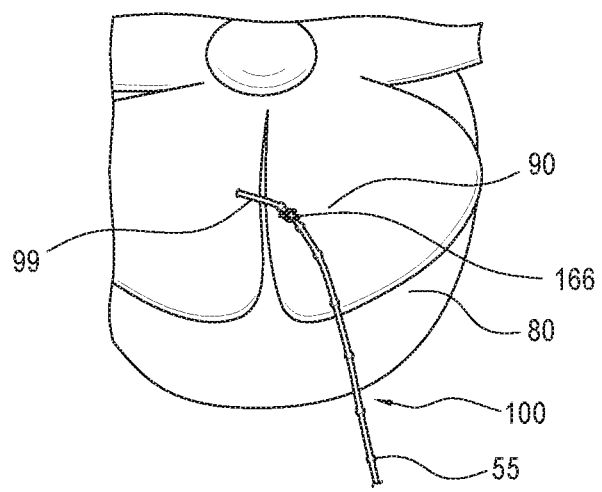
FIG. 7

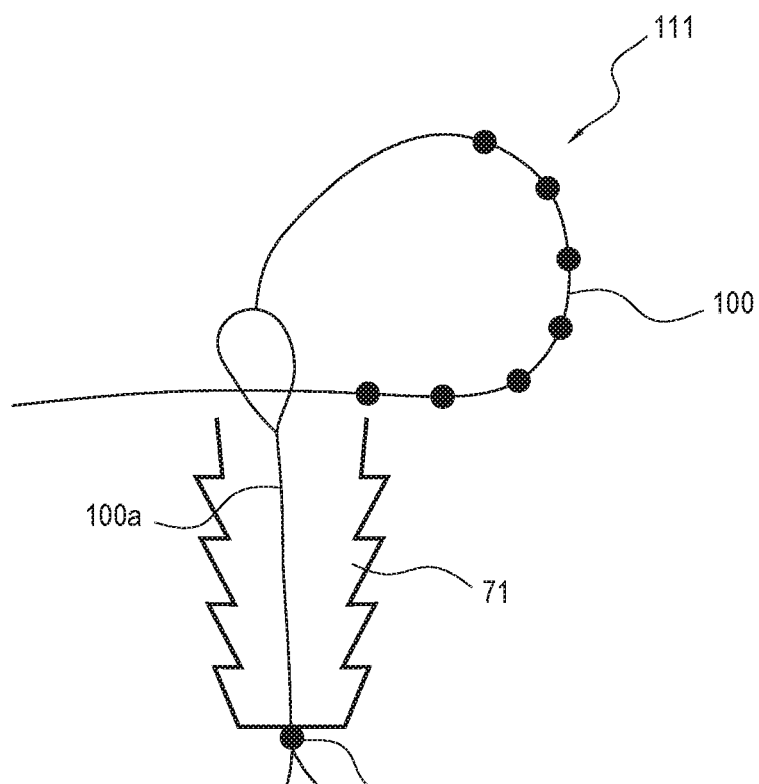
FIG. 20
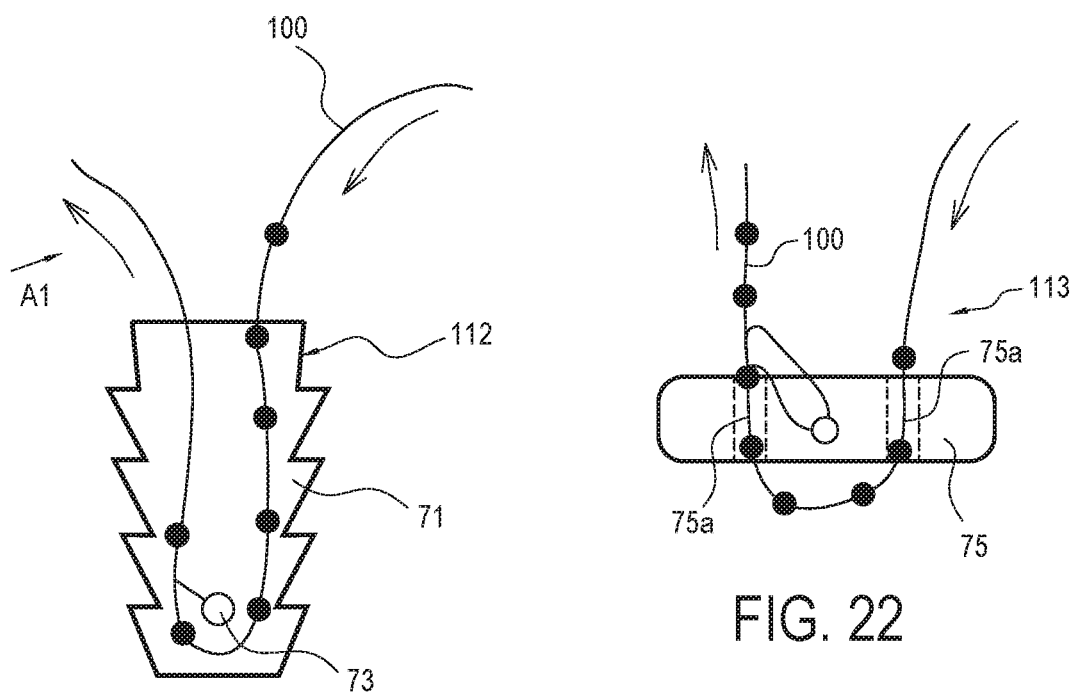
FIG. 21
FIG. 22

KNOTLESS CLOSURE SUTURES AND METHODS OF TISSUE FIXATION

BACKGROUND

The present disclosure relates to the field of surgery and, more particularly, to improved sutures and methods of tissue fixation.

SUMMARY

Suturing constructs and methods for knotless fixation of tissue are disclosed.

A suturing construct may include a bumpy suture. A suturing construct may include one or more small loops on a distal end. A suturing construct may include a splice terminating into a tapered portion/region at a proximal end. A bumpy suture of a suturing construct may form a knotless, closed, self-locking loop around tissue.

Fixation of tissue is achieved by using at least one suturing construct passed around or through tissue (for example, bone or soft tissue). The suturing construct may include a bumpy suture that allows the formation of a closed, knotless, self-locking loop around tissue and locking of the device. The suturing construct may be secured into bone with additional fixation devices (such as one or more suture anchors). The suturing construct may be employed with soft anchors or hard anchors. The construct may be employed with knotless or knotted fixation devices. Tissue fixation is achieved with overall reduced steps and minimal need to tie knots.

BRIEF DESCRIPTION OF THE DRAWINGS

FIG. 4 illustrates an inner strand of exemplary suturing construct of FIG. 1.

FIG. 5 illustrates another view of exemplary suturing construct of FIG. 1.

FIGS. 6 and 7 illustrate subsequent steps of an exemplary method of knotless repair with the suturing construct of FIG. 5.

FIGS. 20-24 illustrate various exemplary suture anchor assemblies.

DETAILED DESCRIPTION

Figure 1:
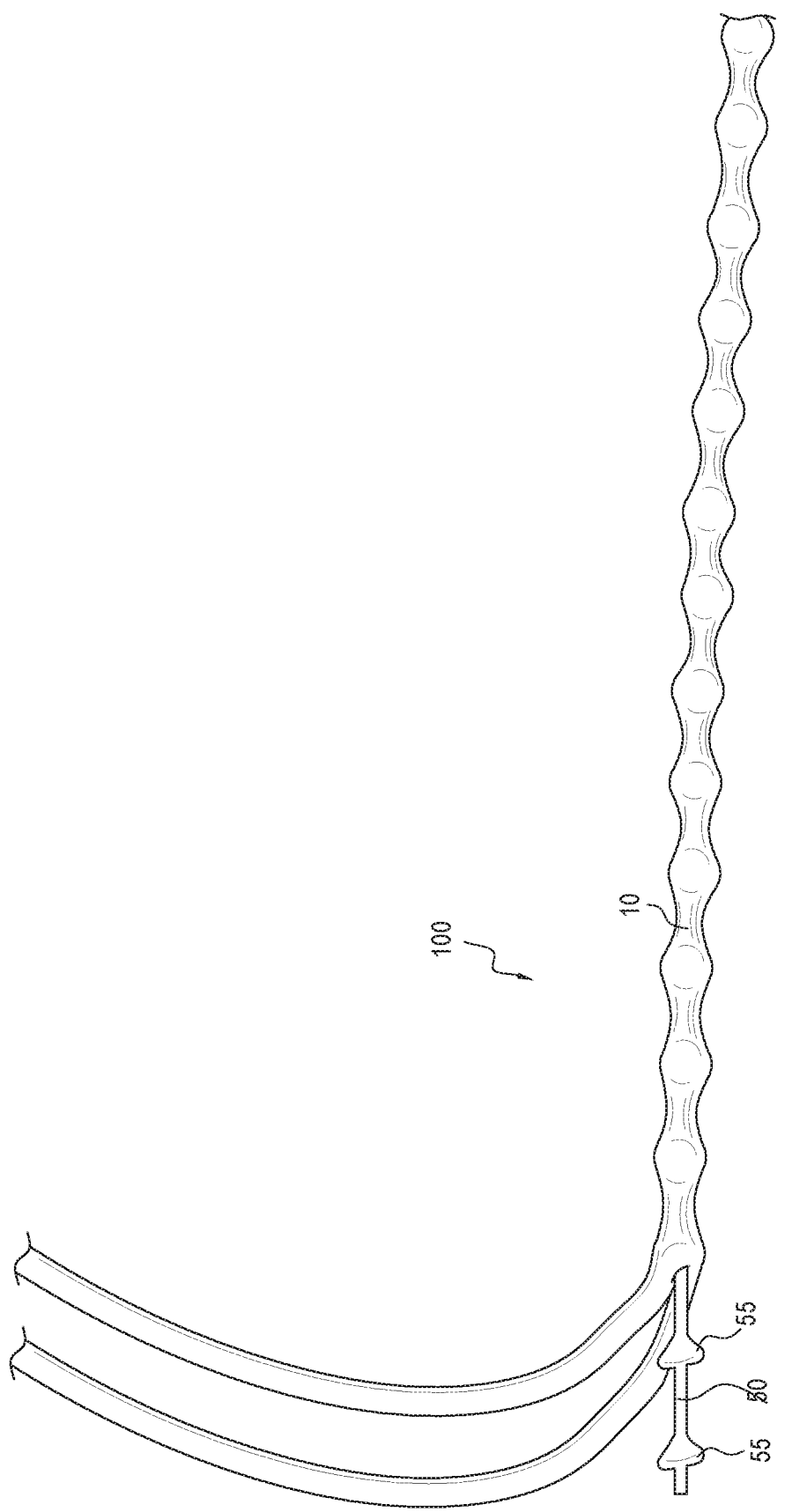
FIG. 1 illustrates an exemplary suturing construct.

The present disclosure provides methods and suturing constructs for fixation of tissue, for example, soft tissue to bone.

Suturing constructs, suture anchor assemblies, and methods for fixation of soft tissue are disclosed. A suturing construct may include a bumpy suture that locks the suture and the repair. A suturing construct may include one or more small loops or apertures on a distal end. A suturing construct may include a splice terminating into a tapered portion/region at a proximal end. A suturing construct may be pre-loaded on a soft suture anchor or a hard-body anchor (fixation device).

A bumpy suture may include a plurality of enlargements which may be a series of bumps, barbs, knots, beads, protuberances, protrusions, ridges, or similar structures (or combinations thereof) which are added as a core to a coreless suture. The enlargements may be knotted and/or provided as a series of bumps (a chain) along an inner filament. The suture may consist of a central strand of core suture (inner filament) with fixed knots, beads and/or ratchets at defined intervals, similar to a bathroom drain chain. The ratchets may be symmetric or asymmetric, with the tapered end towards the cinch. The inner filament with the enlargements may be provided within a coreless suture (for example, inserted into a coreless suture) to form a suture with a bumpy core. The bumps may be knotted bumps to provide at least one ratchet point. The enlargements may be part of an inner strand or filament covered by a coreless suture (outer sheath).

A loop may be provided at one end of a bumpy suture. The bumpy suture may be employed to form a racking hitch (cinch knot) around tissue. The bumpy suture may be employed to form a knotless, closed, self-locking loop around tissue. The enlargements of the suturing construct prevent the suturing construct from sliding back (backing up) once the closed loop has been formed. A splice portion may be provided with the plurality of enlargements in one side near the loop at the distal end of the suture.

Fixation of soft tissue is achieved by using at least one suturing construct passed around or through tissue without the need of nitinol wire loops or similar devices. The tapered portion/region of the construct allows the suture construct to be retrieved after being passed through the tissue. After the formation of a racking hitch or cinch stitch and/or locking with the enlargements portion near the loop, the suture construct may be secured into bone with additional fixation devices (such as one or more suture anchors). The construct may be employed with knotless or knotted fixation devices. Tissue fixation is achieved with overall reduced steps and minimal need to tie knots.

According to one embodiment, a suturing construct may include a suture with enlargements in the form of a series of bumps, barbs, knots, beads, protuberances or similar structures (or any combinations thereof) which are added as a core to a coreless suture. The enlargements may be knotted and/or provided as a series of bumps (a chain) along an inner filament.

The suturing construct may consist of a central strand of core suture with enlargements (i.e., fixed knots, beads, barbs and/or ratchets at defined intervals) similar to a bathroom drain chain. The ratchets may be symmetric or asymmetric, with the tapered end towards the cinch. The inner filament with the enlargements may be inserted into a coreless suture to form a suture with a bumpy core. The enlargements may be knotted bumps to provide at least one ratchet point. The enlargements are part of an inner strand completely covered by a coreless suture (outer sheath). The enlargements are thicker than the coreless suture, i.e., the enlargements have an outer diameter greater than that of the coreless suture.

According to an embodiment, a splice portion may be provided with the plurality of enlargements in one side near the loop at the distal end of the suture. A loader is pre-passed through the loop to load the suture tail back through the loop after passing it through the soft tissue. Once the suture is passed through the soft tissue, the tail is passed through the loop using the loader by folding the tapered end and shuttling it through the loop. The suture is then pulled through until it tightens all the way down. As it tightens, the enlargements that are thicker than the coreless suture pull into the loop and prevent the suture from backing up.

According to another embodiment, a suturing construct may include a flexible strand with one or more small loops or apertures at its distal end, a tapered proximal end (tapered tail), and a splice region provided between the small loops and the tapered proximal end. The splice region is provided with multiple enlargements within a coreless suture (completely covered by a coreless suture) at the distal end of the suture. The enlargements may be any knots, beads, bumps, protrusions, protuberances or similar elements, or combinations thereof. The enlargements may be formed by any methods known in the art, for example, knotting, braiding, weaving or gluing, providing a series of beads on a string, attaching a series of beads or similar elements to a string, etc.

In one embodiment, the suturing construct includes a string of enlargements which are added as a core (bumpy core) to a coreless suture. The enlargements may be knotted, or provided as a series of bumps (a chain), or provided as a series of uni-directional barbs or similar structures, along an inner filament. The enlargements and/or inner filament may be formed of various materials, for example, metal or plastic, or suture materials, among others. The inner filament with the enlargements is provided within (for example, inserted into) a coreless suture to form a suture with a bumpy core.

The enlargements may have various designs and/or configurations, for example, round, triangular, oval or cylindrical cross-sections among many other shapes known in the art. The enlargements may be provided at various locations along the length of the inner filament. The enlargements may be provided in various directions along the length of the inner filament, for example, two-ways enlargements or multiple-ways enlargements. The enlargements may be provided as uni-directional barbs.

In yet another embodiment, the suturing construct may consist of a central strand of core suture with fixed "ratchets" at defined intervals, similar to a bathroom drain chain. The ratchets could be asymmetric with the tapered end towards the cinch (as detailed below). After appropriately defined working distance length, the suture would be the same as a cored #2 FibreWire®, then tapered to a smaller 2.0 FiberWire® to facilitate loading in the cinch mechanism and forming a knotless suture construct with a splice and a splice-forming mechanism. Once the suture is passed through the soft tissue, the tail (tapered end) is passed through the small holes/openings at the distal end by shuttling it through the small holes/openings. The suture is then pulled through until it tightens all the way down. As it tightens, the bumps/ratchets that are thicker engage the small holes/openings and lock the suture under tension, preventing the suture from backing up and from loosening.

A shuttling device may be pre-loaded onto the loop to load the tapered suture tail back through the loop after passing it through the soft tissue. The flexible coreless strand may be suture, tape, wire, or any flexible material known in the art. The shuttling device may be a suture passing instrument, a suture passer, a shuttle/pull device, a loader, a shuttling wire or any passing instrument, such as FiberLink™ or a Nitinol loop. The central core may be suture, tape, wire, or any flexible material known in the art. The central core may be flexible or rigid.

Once the flexible strand is passed through the soft tissue, the tapered tail is passed through a loop of the shuttling device by folding the tapered end and shuttling it through the loop. The flexible strand is then pulled through until it tightens all the way down. As it tightens, the enlargements from the splice portion that is thicker pulls into the loop and prevents the flexible strand from backing up.

The flexible strand may be a standard braided coreless suture, may be tapered, and may include three exemplary varying widths throughout its length, with one or more enlargements/protuberances in one of the portions of the suture to create ridges or bumps. The suture may be provided with a locking mechanism, for example, one or more small loops, eyelets, openings, slits, etc. to allow the suture to be pulled through until the enlargements (ridges/bumps/protuberances/knots) engage and lock the suture under tension.

The loop is large enough to allow the tapered end and part of the splice region to pass through it and then lock to the loop, to create a cinch stitch around soft tissue. The flexible strand may be coreless to allow insertion of the inner filament with enlargements or, in certain applications, portions of the coreless strand may have a core. The loop may be formed by splicing or by other methods known in the art, for example, braiding, weaving or gluing.

In another embodiment, a suture zip-tie includes a coreless suture or overbraided jacket that houses (completely covers) an inner core, which is a smaller suture with enlargements (knots/beads/barbs etc.). The suture may terminate in a loop to allow formation of at least one racking hitch. The enlargements provide ratchet points to keep the racking hitch from slipping.

Referring now to the drawings, where like elements are designated by like reference numerals, FIGS. 1-19 illustrate exemplary suturing constructs 100, 200, 300, 400 (suture 100, 200, 300, 400; suture construct 100, 200, 300, 400; side-to-side knotless suture 100, 200, 300, 400; knotless closure suture 100, 200, 300, 400) of the present disclosure. FIGS. 20-28 illustrate suturing constructs 100, 200, 300, 400 as part of suture anchor assemblies 111, 112, 113, 114, 115, 116, 117 employed for fixation of first tissue to second tissue.

As detailed below, each of the suturing constructs 100, 200, 300, 400 includes a central strand of core suture 50 (first strand or filament; inner strand) and an outer strand of suture 10 (second strand or filament; outer strand; coreless suture) covering the central strand. The central strand 50 includes a plurality of enlargements 55, 155, 255, 355. In an embodiment, the outer strand 10 covers completely the central strand 50 and enlargements 55, 155, 255, 355 in at least two directions, a longitudinal direction and a transversal direction.

The enlargements 55, 155, 255, 355 may include bumps, knots, beads, barbs, protrusions, or protuberances, or any combinations thereof. Enlargements 55, 155, 255, 355 may have various designs and/or configurations, for example, round, oval or cylindrical among many other shapes known in the art. The enlargements may be provided at various locations along a length of the inner filament 50 (central strand 50). The enlargements may be provided at various locations along a predetermined length of the inner filament 50 (i.e., along only a portion of the length of the central strand 50). The enlargements may be provided in various directions along the length of the inner filament, for example, two-ways enlargements wherein a first plurality of enlargements are oriented in a first direction relative to a longitudinal axis of strand 50 and wherein a second plurality of enlargements are oriented in a second direction relative to the longitudinal axis of strand 50, the first direction being different from the second direction. The enlargements may be formed at any angle with the surface of the central strand, for example, at a 45 degree angle with the tangent to an outer surface of the central strand. The enlargements may be all similar or different, i.e., may be have similar or different shapes, forms and configurations. The enlargements may be all formed of similar or different materials.

FIG. 1 illustrates an exemplary-only embodiment of the present disclosure, wherein suturing construct 100 includes central strand 50 with enlargements 55 having a general trapezoidal shape and extending along a length of the central strand 50 at about regular intervals. Enlargements 55 may extend along the whole length of the inner strand 50, or along only a portion of the length of the inner strand 50. Outer suture 10 is a coreless suture (coreless strand) that covers the central strand 50 and the enlargements 55. Outer suture 10 is a coreless suture (coreless strand) that completely covers the central strand 50 with enlargements 55 in at least a transversal direction, i.e., the outer surface of each enlargement 55 is completely covered by outer suture 10. Preferably, outer suture 10 covers the central strand 50 with enlargements 55 in two directions, i.e., in both longitudinal and transversal directions. Central strand 50 with enlargements 55 may be provided within the inner space/volume of the coreless suture 10 (by being inserted within the coreless suture 10, for example) to form suturing construct 100 (with the coreless suture 10 not being coreless subsequent to the insertion step). Once the inner strand 50 with enlargements 55 has been provided within the outer strand 10, the outer strand 10 will acquire a "bumpy" feel, as the enlargements will exert pressure along the inner surface of the outer strand 10 but without penetrating the outer surface of the outer strand 10.

Figure 2:
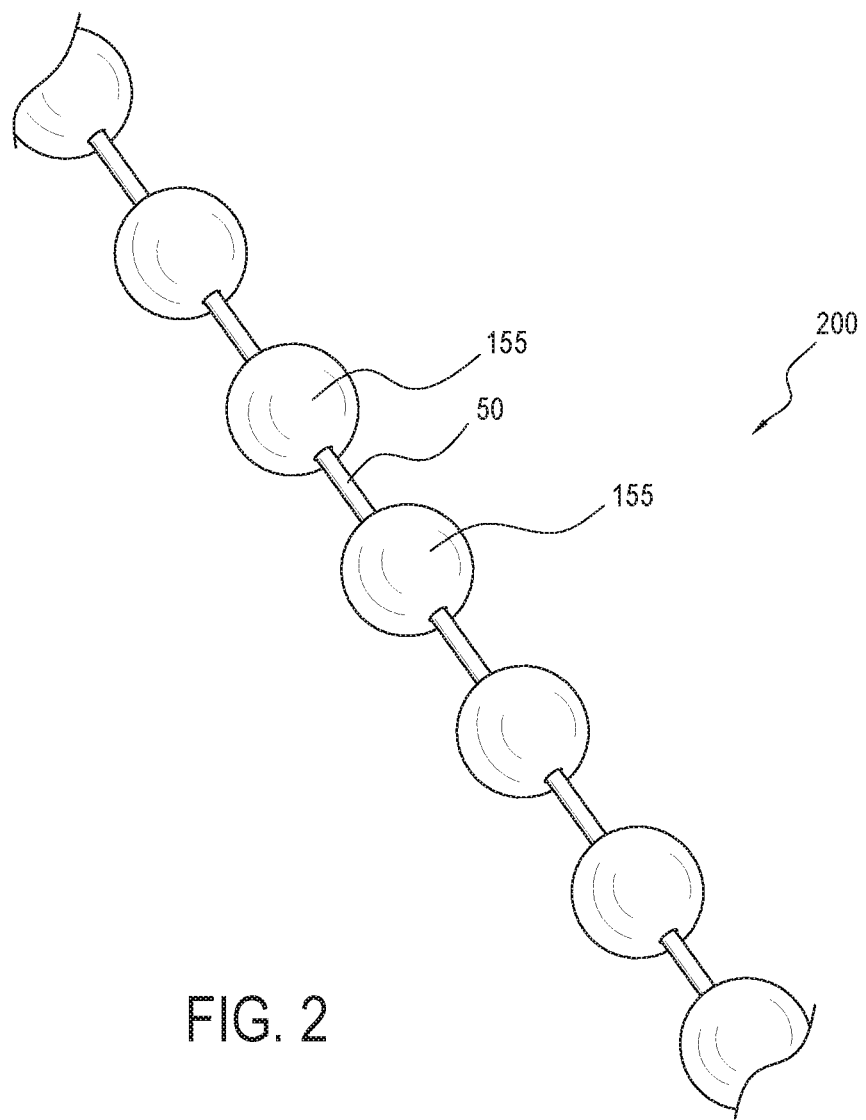
FIG. 2 illustrates another exemplary suturing construct.
Figure 3:
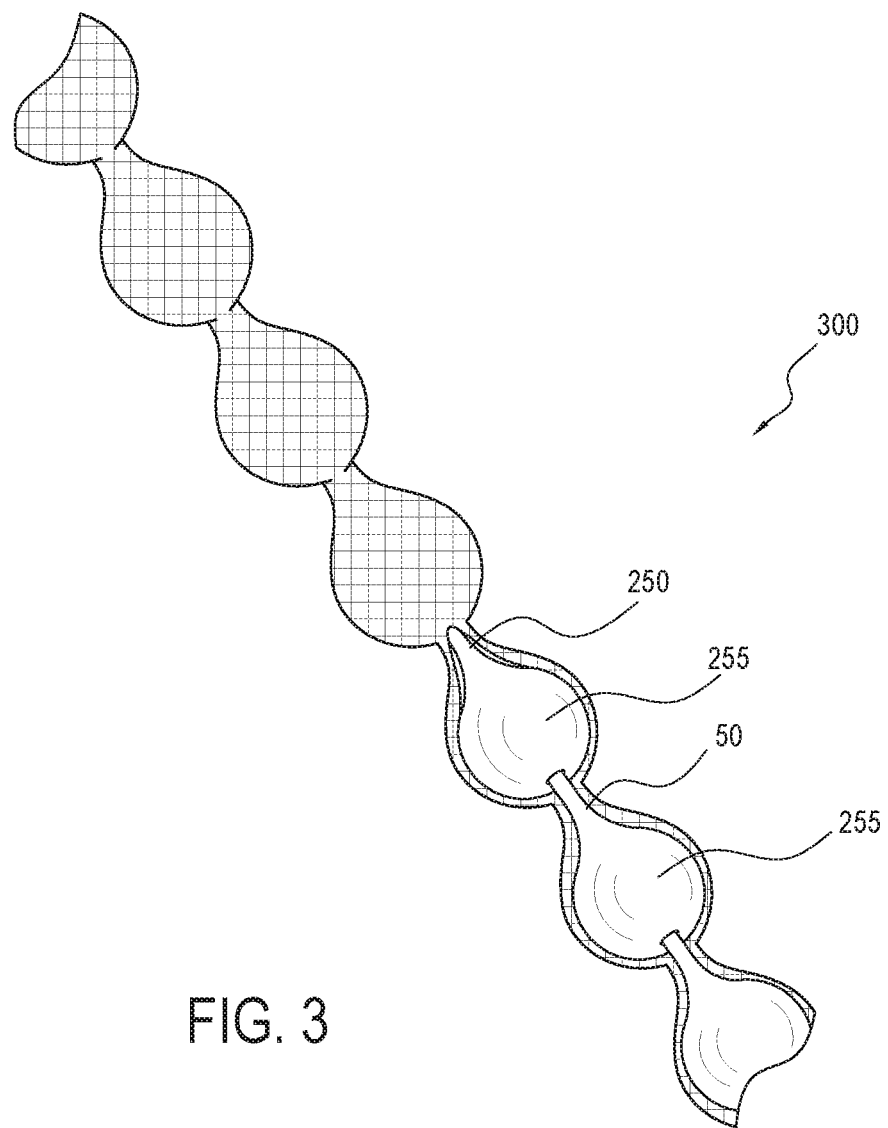
FIG. 3 illustrates another exemplary suturing construct.

FIGS. 2 and 3 illustrate suturing constructs 200, 300 with enlargements 155, 255 which are similar to enlargements 55 of FIG. 1 in that they are also spaced apart along a length of suture 50 and are completely covered by outer sheath 10 but differ in the shape of the enlargements. For example, enlargements 155 are in the form of beads or spherical structures, while enlargements 255 are in the form of tear drop-shaped structures. Enlargements 255 are fixed "ratchets" at defined intervals along inner strand 50, similar to a bathroom drain chain. The ratchets could be asymmetric with the tapered end towards the cinch (as detailed below). After appropriately defined working distance length, the suture would be the same as a cored #2 FibreWire®, then tapered to a smaller 2.0 FiberWire® to facilitate loading in the cinch mechanism and forming a knotless suture construct with a splice and a splice-forming mechanism. Once the suture is passed through the soft tissue, the tail (tapered end) is passed through the small holes/openings at the distal end by shuttling it through the small holes/openings. The suture is then pulled through until it tightens all the way down. As it tightens, the bumps that are thicker engage the small holes/openings and lock the suture under tension, preventing the suture from moving in any direction.

FIGS. 4-7 illustrate suturing construct 400 with enlargements 355 in the form of knots 355 extending along central strand 50 (FIG. 4). Inner core 50 shown in FIG. 4 is a smaller suture provided with knots 355. Coreless suture or over-braided jacket 10 (outer strand 10) covers the inner core 50. Outer strand 10 completely covers inner central strand 50 with knots 355 to form suturing construct 400 shown in FIG. 5.

The fixation/interference of the enlargements may be achieved in a variety of ways and with various locking structures. For example, and as shown in FIGS. 5-7, exemplary suturing construct 400 is provided with a loop 11 for creating a racking hitch 166. The knots 355 (knot bumps 355) provide ratchet points to prevent the racking hitch from slipping. FIG. 7 illustrates a schematic view of a final repair with suturing construct 400 with enlargements 355 locked into place by racking hitch 166, i.e., unable to slip or slide out of the loop formed around first tissue 90 (for example, soft tissue 90) attached to second tissue 80 (for example, bone 80).

Figure 28:
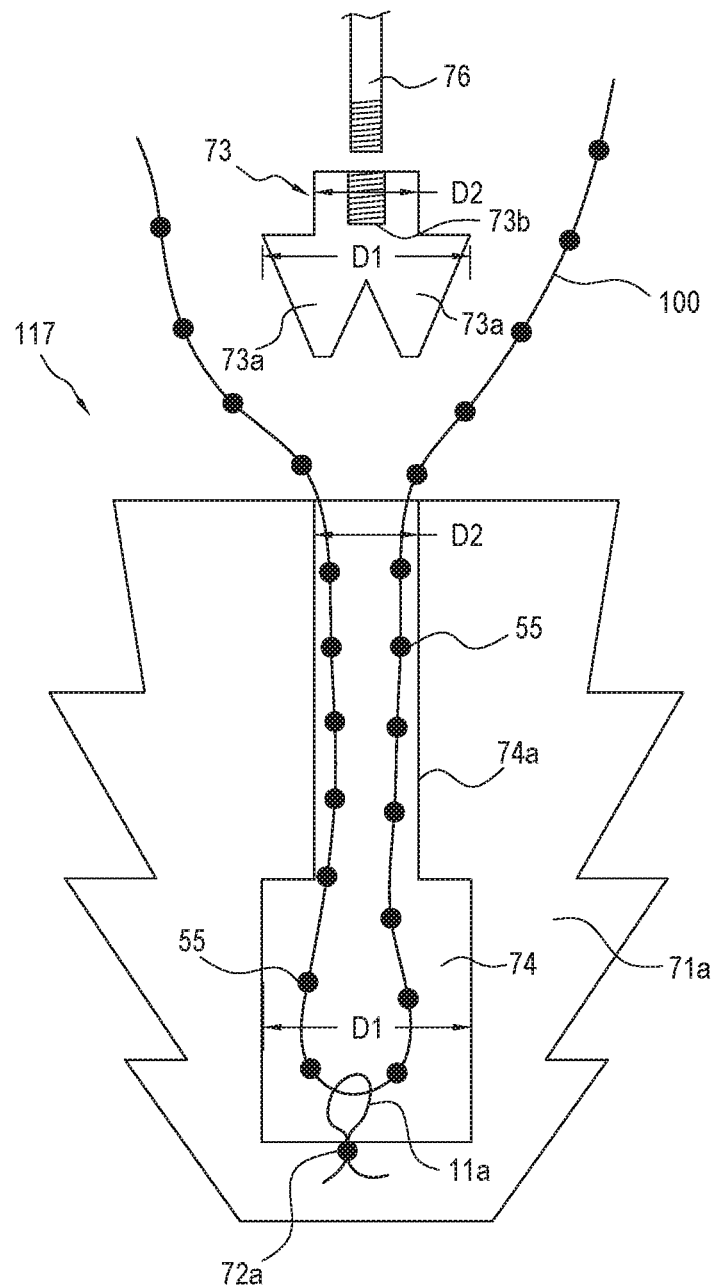
FIG. 28 illustrates another exemplary suture anchor assembly.

Loop 11 may be formed integrally to, or separate from, the suturing construct. Loop 11 may be part of outer strand 10 or, alternatively, part of inner strand 50. In yet another embodiment, loop 11 may be part of both strands 10, 50. In additional embodiments, loop 11 may be attached to the suturing construct (for example, to one or both of the outer and inner strands) by any methods known in the art. For example, FIG. 28 illustrates an exemplary loop 11a attached to exemplary construct 100 and further securely attached to a hard body of a knotless fixation device. In yet another embodiment, outer strand 10 is spliced into itself to form small loop 11 (or a double loop) and a splice. Small loop 11 may be integral to the suture strand 10.

Fixation/interference of the enlargements may be achieved in other ways, for example, in any way wherein enlargements 55, 155, 255, 355 may be locked in, such as pre-tied knots, or slits, or any "eyelet" that would provide a tight interference to and with the enlargements.

Figure 8:
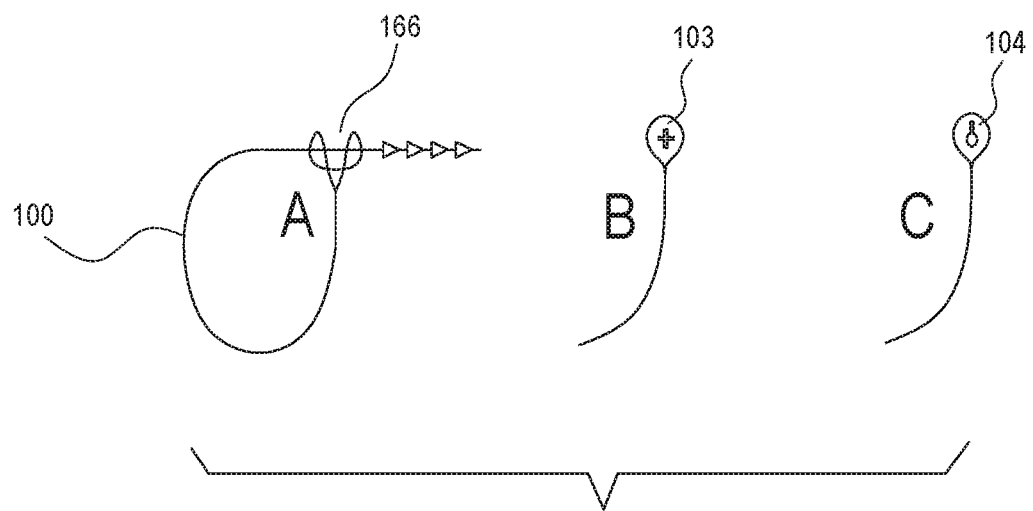
FIG. 8 illustrates schematic steps of forming a knotless loop with an exemplary suturing construct.

FIG. 8 illustrates exemplary suturing construct 100 that is passed through a pre-tied knot 166 of structure A that can be part of construct 100, for example, part of outer strand 10. Pre-tied knot 166 is a point of interference for the enlargements (bumps, beads, etc.) to "catch on." Structure A is a racking hitch knot. Structures B and C provide additional interference points, similar to the pre-tied knot of structure A (in that they also "catch on" any enlargements/bumps/beads passing there through) but having different configuration, i.e., a slit 103 (structure B) or a small eyelet 104 (structure C).

Figure 9:
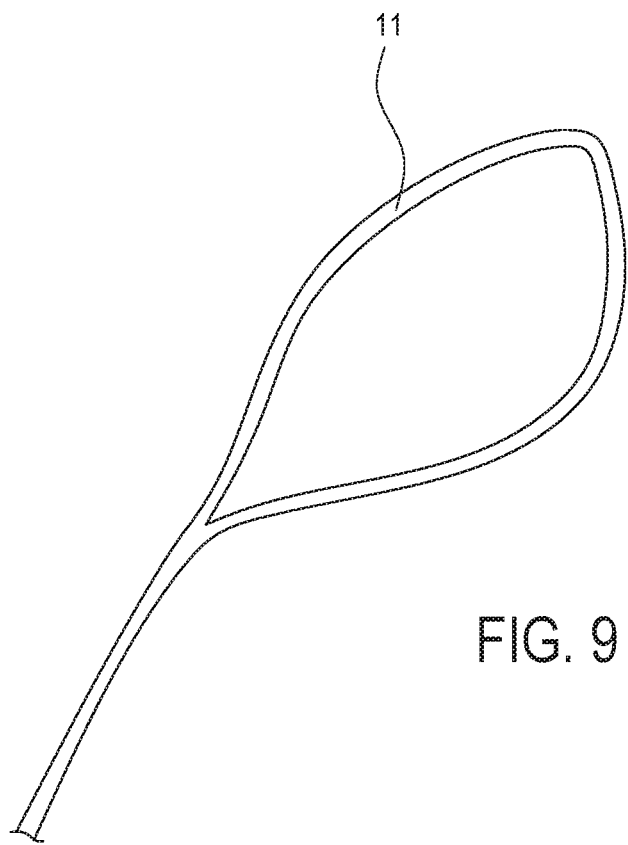
FIGS. 9-11 illustrate subsequent steps of an exemplary method of forming a knotless, closed, self-locking loop with a suturing construct.
Figure 10:
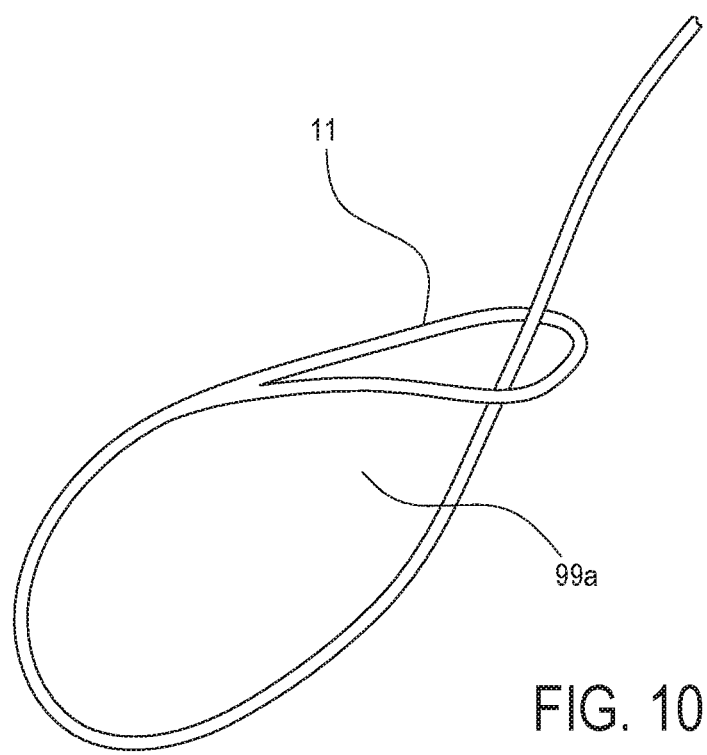
Figure 11:
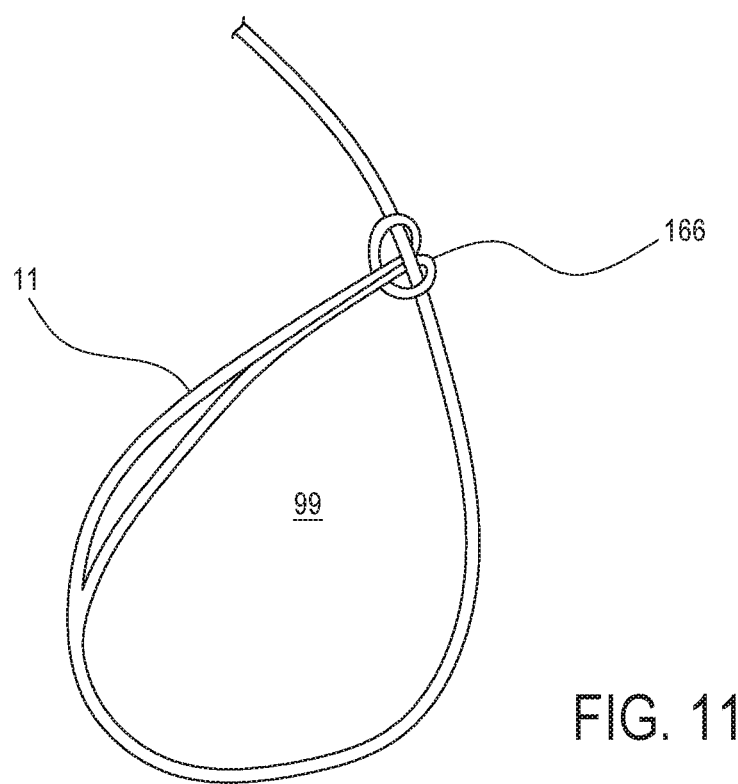
Figure 12:
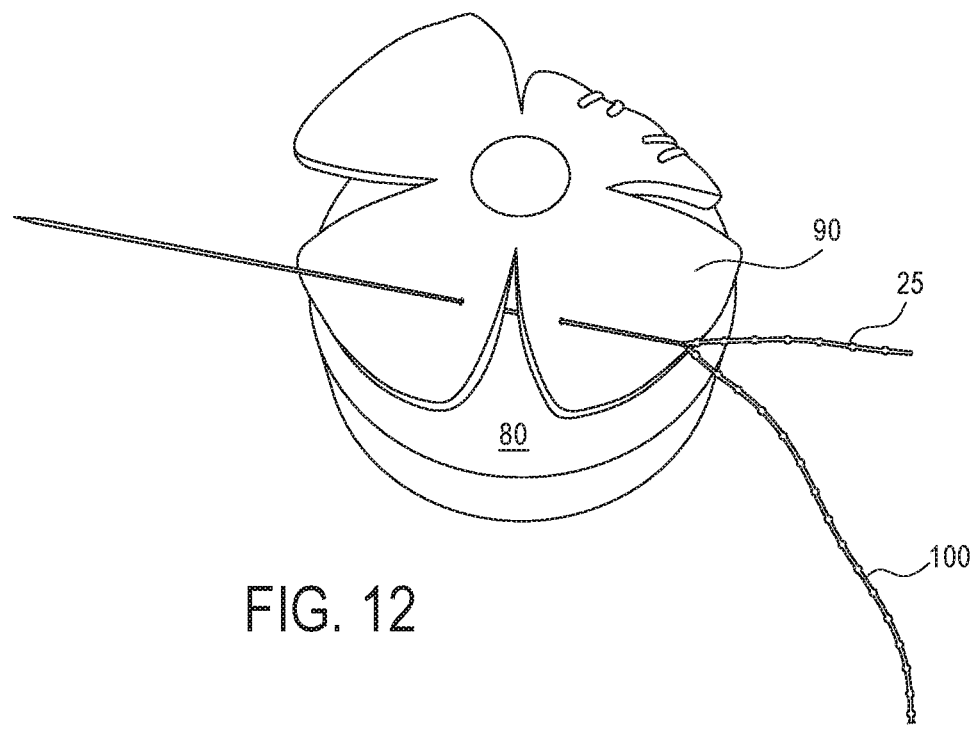
FIGS. 12-15 illustrate subsequent steps of an exemplary method of knotless repair with a suturing construct.

FIGS. 9-11 illustrate the formation of a closed, self-locking loop 99 formed with a construct of the present disclosure. FIG. 9 is an enlarged view of loop 11 of FIG. 5 to allow formation of a racking hitch knot. The hitch is created by starting with loop 11 which is pre-made at the end of the suture, or formed by doubling over a single strand. In FIG. 10, the tail(s) are passed through the loop 11 to create a "luggage tag" type cinch knot which becomes the pre-tied knot 166 and forms loop 99a.

Referring now to FIG. 11, the tails are passed through the pre-tied racking/cinch knot 166. A close, self-cinching and self-locking loop 99 is formed. As detailed below, the loop may be formed around bone or soft tissue. The tighter the large loop is pulled closer to tissue, the tighter the racking/cinch knot will close around the suture limb(s) passing through it. This is where the bumpy suture passes through but the enlargements/bumps would prevent the suture from sliding back (like a zip tie). The enlargements/bumps allow the construct to become "self-locking" and prevent the suturing construct from moving in any direction.

Figure 13:
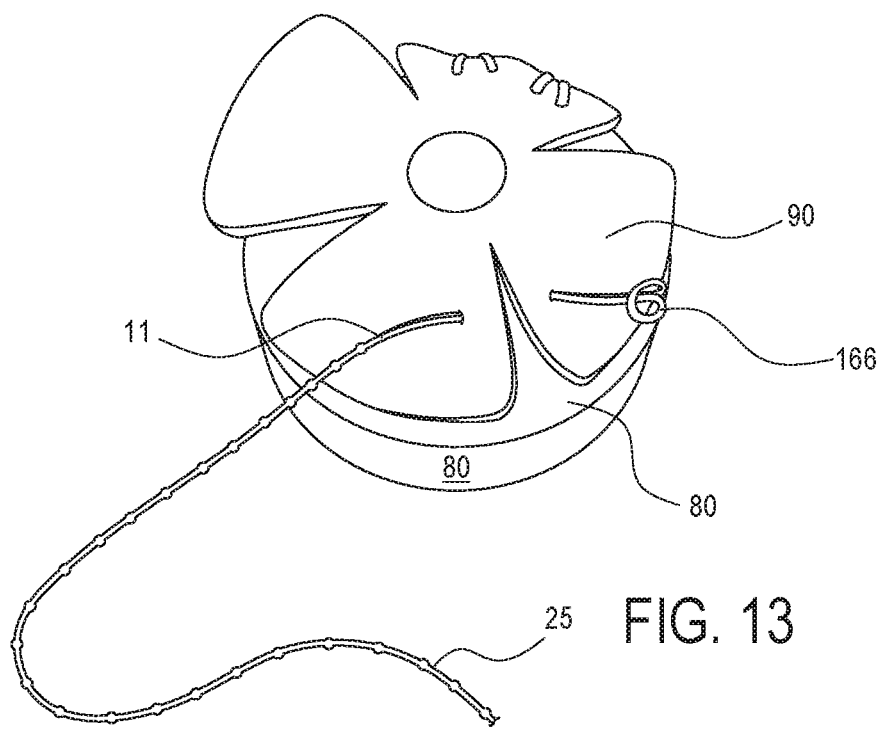
Figure 14:
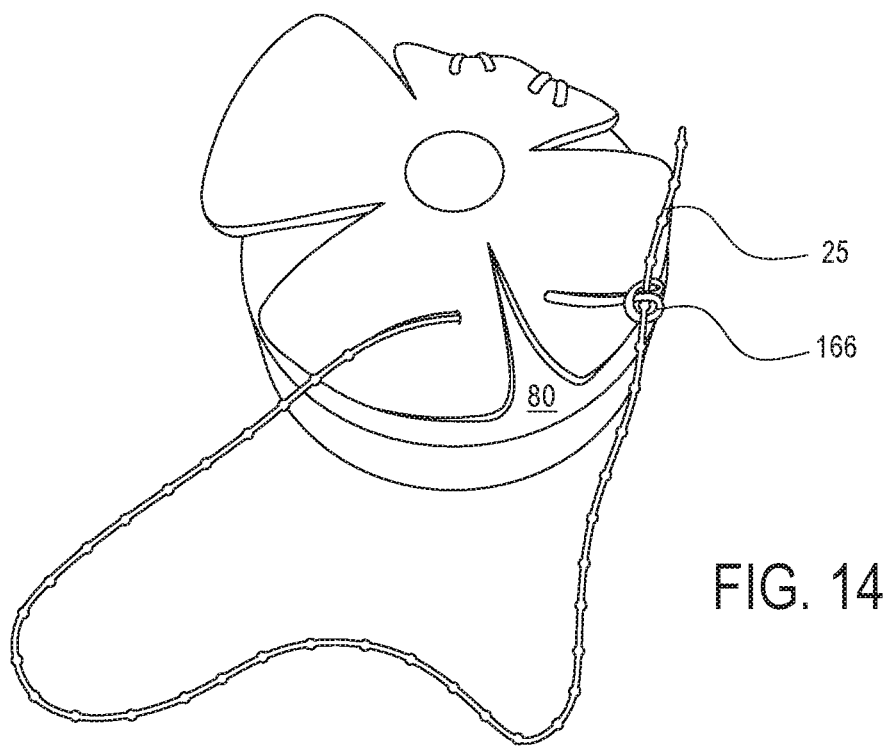
Figure 15:
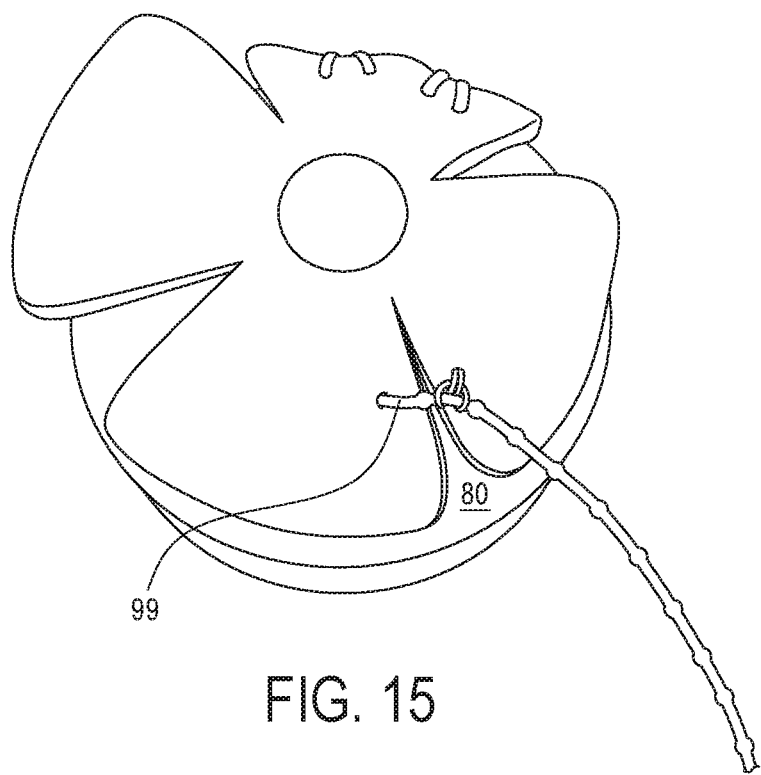

FIGS. 12-15 illustrate subsequent steps of a method of tissue fixation with the constructs of the present disclosure. Suturing construct 100 is passed through a first tissue 90 to be attached to a second tissue 80 (for example, soft tissue 90 to be attached to bone 80). FIG. 13 illustrates racking/cinch knot adjacent first tissue 90. Tail 25 is passed through the racking/cinch knot to form closed, adjustable, self-locking, self-cinching, knotless flexible loop 99 around tissue 90 to be attached to tissue 80.

Figure 16:
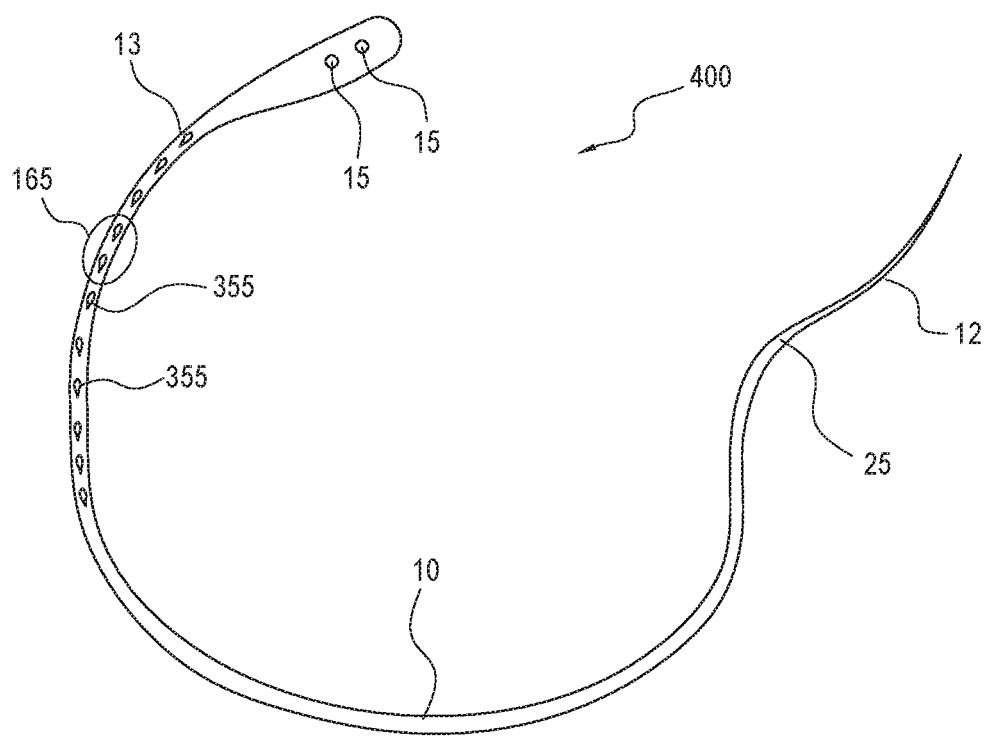
FIG. 16 illustrates another exemplary suturing construct.
Figure 17:
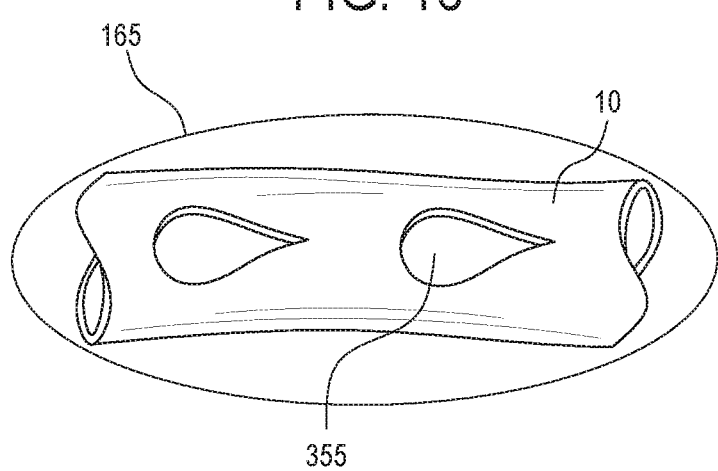
FIG. 17 illustrates an enlarged view of section A of the exemplary suturing construct of FIG. 16.

FIGS. 16 and 17 illustrate another exemplary embodiment of construct 400 in the form of a flexible strand 10 provided with at least one small closed loop 15 (for example, two exemplary small closed loops 15) at one end 13 (for example, distal end) and with a tapered elongated portion/region 25 at other end 12 (for example, proximal end). Enlargements 355 are provided on enlargement portion (cinch section) 165 of the construct 400, as detailed above with respect to the previously-discussed embodiments. FIG. 17 illustrate a schematic enlarged view of section A of FIG. 16, illustrating enlargements 355 having a specific configuration, an elongated tear drop-shape. Enlargements 355 are completely covered by coreless suture strand 10 so that the outer surface of each of enlargements 355 is completely covered by inner surface of the strand 10.

Suturing construct 100, 200, 300, 400 of the present disclosure may be also provided with a shuttling device 60 which may be a suture passing instrument, loader, shuttling wire or passing instrument, such as FiberLink™ 60 or a Nitinol loop 60 with closed loop or eyelet 61 attached to the outer strand 10 of the suturing construct.

Figure 18:
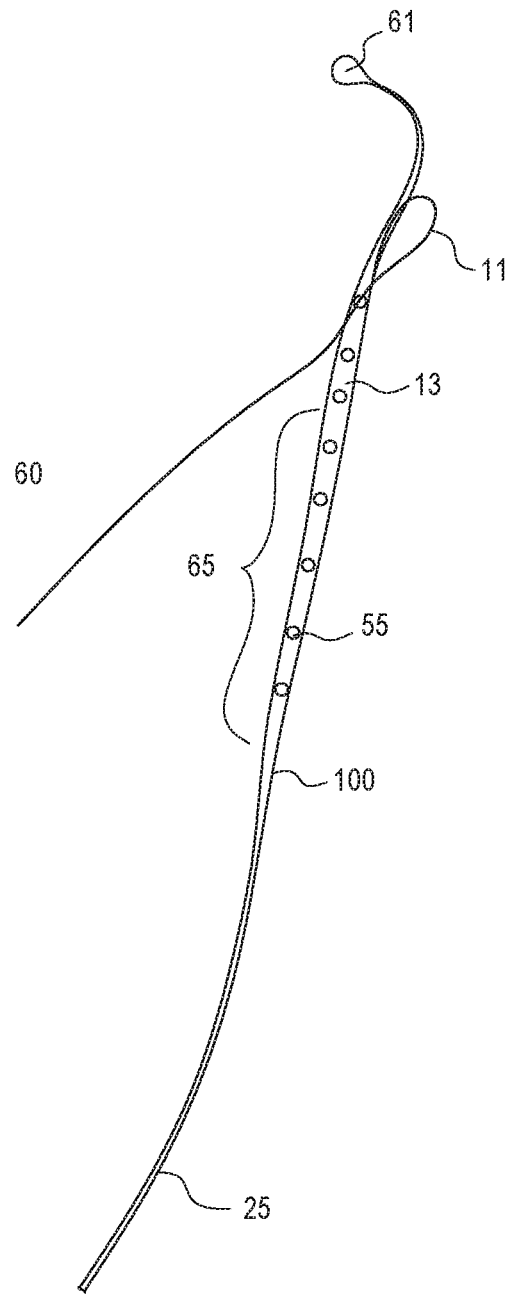
FIG. 18 illustrates another view of exemplary suturing construct of FIG. 1 with a shuttling device.

As shown in FIG. 18, shuttling device 60 is pre-loaded onto closed loop 11 (threaded through the closed loop 11) of exemplary suturing construct 100. In particular and exemplary-only embodiments, the shuttling device 60 is a suture passing device 60. The shuttling device 60 is configured to allow the tapered portion 25 of the outer strand 10 to pass through eyelet or loop 61 of the shuttling device 60 and through the small loop 11, to form a knotless closed adjustable loop 99 having an adjustable length and perimeter. Loop 99 is self-locking and self-cinching.

Suturing construct 100 includes a series of enlargements 55 that may be located in one side near the loop 11 at the distal end 13 of the outer strand 10, i.e., on or around portion 65 (cinch section 65; splice section 65). The enlargements (bumps and/or barbs and/or ridges and/or protuberances) roughen the outer strand 10 (suture 10) for knotless locking. Once the outer strand 10 is passed through the soft tissue, the tail 25 is passed through the loop 61 using the loader 60 by folding the tapered end 25 and shuttling it through the loop 11. The flexible strand 10 is then pulled through until it tightens all the way down. As it tightens, the thicker enlargement roughened portion 60 with enlargements pulls into the loop 11 and prevents the flexible strand 10 from backing up. In this manner, flexible closed adjustable loop 99 is locked by the engagement of enlargements 55 with inner surface of loop 11.

In an exemplary embodiment, loop 11 has a very small length and/or perimeter to allow the tail 25 to pass through the loop and form a closed, knotless, adjustable loop 99. Loop 11 may have a length of about 10 mm. The tapered portion/region 25 has a length of about 2-3 inches. The overall length of the suture construct may be about 3 to 10 inches, preferably about 5 inches (for exemplary rotator cuff repairs involving attachment of labrum to glenoid). The loop portion is formed by splicing (in the preferred embodiment) but it could be also formed by other methods known in the art, for example, by braiding, weaving or gluing. The loop 15 may be flexible, collapsible and with a fixed perimeter of about 10 mm.

As detailed above, the loop 11 may be also a racking hitch loop. Tail 25 is passed/loaded through small loop 11 of flexible strand 10, as shown in FIG. 3, for example. The tail is pulled through until a small opening is left (FIG. 4). A suture loader 60 is added, to pull the tail through the racking hitch after it is passed through the tissue.

In an exemplary embodiment, the flexible strand 10 of suturing construct 100, 200, 300, 400 is suture formed essentially of a braid such as a FiberWire® CL braid, which is a coreless braid with ultrahigh molecular weight polyethylene (UHMWPE). In another exemplary embodiment, the outer strand 10 is a suture formed essentially of polyester or similar material. For example, the outer strand 10 may be formed of polyester yarns (twisted yarns of polyester) or a polyester suture in the form of a coreless braid or sheath which may be a multifilament, braided, knitted, or woven polyester construct, wherein the polyester is provided alone or in combination with any other known suture materials. In an exemplary-only embodiment, the outer strand 10 is a braided coreless suture with about 100% polyester.

At least one or all of suture sections of exemplary suturing construct 100, 200, 300, 400 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the final suture construct, knot security, pliability, handleability or abrasion resistance, for example.

The elongated tapered region 25 of the surgical constructs of the present disclosure allows the flexible strand/suture to be pushed through small and very small diameter tubes and cannulations (such as Lasso instruments, for example) yet fix securely with fixation devices (such as knotless suture anchors like PushLock® anchors).

Surgical suturing construct 100, 200, 300, 400 may have cross-sections of various forms and geometries, including round, oval, rectangular, or flat, among others, or combination of such forms and geometries. The diameter of construct 100, 200, 300, 400 may be constant or may vary. Tapered region 25 may include a plurality of adjacent tapered regions, each of the regions having a diameter different from those of the adjacent regions. In an exemplary-only embodiment, region 25 may comprise three adjacent regions, each having a taper different from the adjacent regions.

At least a part of the fibers of suturing construct 100, 200, 300, 400 may contain strands of a high strength suture material, such as Arthrex FiberWire† suture disclosed in U.S. Pat. No. 6,716,234, the disclosure of which is incorporated in its entirety by reference herein, with optional colored strands to assist surgeons in distinguishing between various suture lengths.

Surgical suturing constructs 100, 200, 300, 400 have applicability (by themselves or in any combination) to suture applications that may be employed in surgical procedures such as rotator cuff repair, Achilles tendon repair, patellar tendon repair, ACL/PCL reconstruction, hip and shoulder reconstruction procedures, and applications for suture used in or with suture anchors. In exemplary embodiments only, the suturing constructs 100, 200, 300, 400 may be employed in suture applications that do not involve knot tying, for example, for use with suture anchors (such as PushLock® and/or SwiveLock® suture anchors) or for knotless arthroscopic suture repairs (such as knotless single row rotator cuff repair, or SpeedBridge™ repair using no knots and only suture passing steps), among many others, but with simplified steps as no nitinol wires or similar structures are required.

In an exemplary-only embodiment, one or more constructs 100, 200, 300, 400 are employed to bring together a first tissue portion (for example, a first soft tissue) to a second tissue portion (for example, a second soft tissue) in a side-to-side closure repair. The construct is first passed through the first tissue portion. The tail (tapered region 25) is passed through or around the second tissue portion, and then passed through a locking structure/mechanism/device (e.g., a loop, eyelet, slit, or combinations thereof) using the shuttling device (loader) by folding the tapered end 25 and shuttling it through the locking structure. Flexible strand 10 (suture 10) is then pulled until it tightens and achieves the desired tension on closed adjustable loop 55. As the flexible strand 10 tightens, the enlargement portion 65, 165 of the construct 100, 200, 300, 400 (that is thicker) pulls into the locking mechanism (loop 11, 15, 166, 103, 104) and locks enlargements 55, 155, 255, 355 to the inner surface of loop 11, 15, 166, 103, 104 (to the flexible strand 10) to prevent the outer strand 10 from backing up. In an exemplary embodiment, the enlargements are a plurality of ridges/bumps/barbs/protuberances that engage and lock the suture 10 under tension. The outer strand may be a standard braided suture that is tapered and that has three varying widths throughout its length. The outer strand may be flexible. The outer strand 10 may be flexible before and after inner core 50 with enlargements 55, 155, 255, 355 is provided within the outer strand 10. The inner strand 50 may be rigid or flexible.

Figure 19:
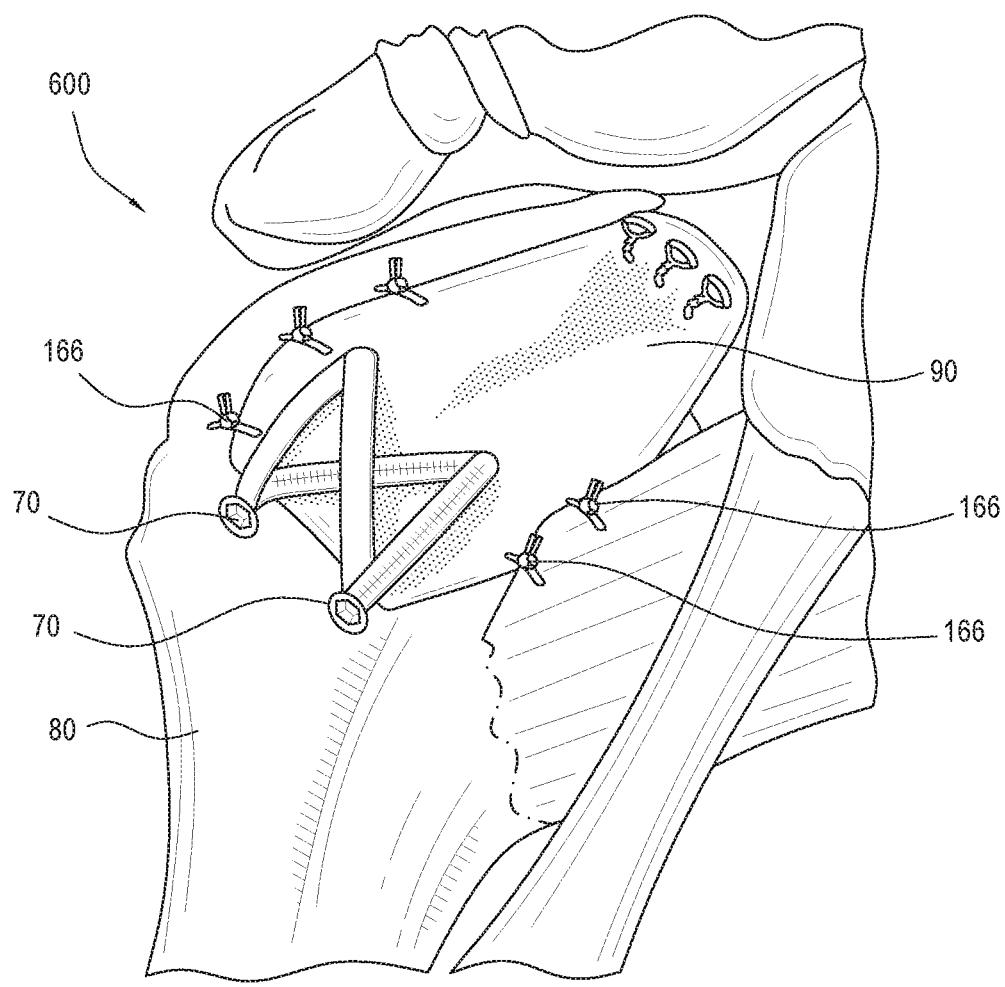
FIG. 19 illustrates a shoulder repair with a suturing construct.

FIG. 19 illustrates a schematic view of a surgical site undergoing a method of fixation of soft tissue to bone (or of soft tissue to soft tissue) by the methods of the present disclosure. In an exemplary embodiment only, the surgical site is the shoulder and the tissue is labrum 90 to be attached to glenoid 80 with exemplary surgical construct 100. Although, for simplicity, the embodiments below will be described with reference to exemplary construct 100, the disclosure has applicability to any of surgical constructs 100, 200, 300, 400 (employed by themselves, alone or in any number, and also employed in any combination of these surgical constructs).

Fixation of soft tissue to bone, such as fixation of labrum to glenoid, typically involves the formation of an incision to access the surgical site and then reattachment of the soft tissue. When soft tissue is attached to bone, the surgeon drills a cavity in the bone and inserts a fixation device such as a bone anchor. Typically, the bone anchor is formed of metal, composite, plastic or bioabsorbable material, and is held in place by threads or by barbs. If an anchor is employed, the anchor typically includes an eyelet through which construct 100 is then threaded/passed.

After the formation of cinch stitch (FIG. 19) and the locking of the construct with enlargements 55, 155, 255, 355 penetrating inner surface area of loop 11, the suturing construct 100 may be secured into bone 80 with one or more fixation devices (such as one or more suture anchors like anchors 70 of FIG. 19) by passing tapered end region 25 through an eyelet of the anchor (not shown) and then securing the knotless fixation device 70 with suturing construct 100 in bone, to obtain final repair 600 (FIG. 19).

The flexible strands may be also secured by employing any number of fixation devices, knotless or otherwise, for example two fixation devices such as two knotless fixation devices 70 with two eyelets, In lieu of the one fixation device. The technique may be repeated multiple times at different locations in the bone (i.e., multiple cinch stitches at different locations around the labrum).

A method of fixation of a first tissue to a second tissue with suturing construct 100, 200, 300, 400 comprises inter alia the steps of: (i) passing a suturing construct 100, 200, 300, 400 through or around the first tissue, the suturing construct comprising an outer strand 10 housing an inner strand 50 with a plurality of enlargements 55, 155, 255, 355; and (ii) locking the suturing construct by forming a cinch looped around tissue and locking at least one enlargement 55, 155, 255, 355 to an inner surface of a locking structure 11, 15, 166, 103, 104. The method may further comprise the steps of (iii) attaching the suturing construct 100, 200, 300, 400 to a knotless fixation device 70; and (iv) placing the knotless fixation device 70 with the attached suturing construct 100, 200, 300, 400 into a second tissue. The method may further comprise the step of (v) threading a tapered end 25 of the suturing construct 100, 200, 300, 400 through an eyelet of the knotless fixation device. The eyelet may be closed (closed opening) or open (i.e., forked opening).

A method of fixation of a first tissue to a second tissue with suturing construct 100, 200, 300, 400 comprises inter alia the steps of: (i) passing a suturing construct 100, 200, 300, 400 through or around the first tissue, the suturing construct consisting of a length of an outer strand 10 having a first end and a second end, a locking structure 11, 15, 166, 103, 104 formed at the first end, a tapered region 25 formed at the second end, a splice/enlargement region 65, 165 located adjacent the first end and the locking structure 11, 15, 166, 103, 104 wherein the enlargement region (or a region adjacent the locking structure 11, 15, 166, 103, 104) includes a plurality of enlargements that prevent the outer strand 10 from backing up, and a shuttling device 60 with a shuttling loop 61 attached to the outer strand 10; (ii) passing the tapered end 25 of the flexible strand through shuttling loop 61; and (iii) pulling the shuttling device to allow the flexible strand to form a cinching loop 99 around tissue 80, 90 and to lock the enlargements 55, 155, 255, 355 to an inner surface of locking structure 11, 15, 166, 103, 104. The method may further comprise the steps of (iv) attaching the suturing construct 100, 200, 300, 400 to a knotless fixation device 70 by threading the tapered end 25 of the suturing construct 100, 200, 300, 400 through an eyelet of the knotless fixation device; and (v) placing the knotless fixation device 70 with the attached suturing construct 100, 200, 300, 400 into a second tissue.

The suturing constructs 100, 200, 300, 400 may be employed in surgical procedures such as rotator cuff repair, Achilles tendon repair, and patellar tendon repair, among many others. Although the invention has been described with reference to a particular application (i.e., fixation of labrum to glenoid in a shoulder repair), it must be understood that the suture constructs of the present invention have applicability to any type of repairs (any repair in addition to a shoulder repair) and, thus, the invention is not limited by this exemplary-only embodiment.

In an exemplary embodiment only, the fixation device 70 is a knotless suture anchor such as the two-piece Arthrex PushLock® anchor, disclosed in U.S. Pat. No. 7,329,272, or an Arthrex SwiveLock® anchor, disclosed in U.S. Pat. No. 8,012,174 issued Sep. 6, 2011, U.S. Pat. No. 9,005,246 issued Apr. 14, 2015, and US 2013/0296936 published Nov.

7, 2013, the disclosures of all of which are fully incorporated by reference in their entirety herein.

The suturing constructs 100, 200, 300, 400 may be also employed with knotted fixation devices, for example, knotted anchors. Thus, the disclosure is not limited to the use of suturing constructs 100, 200, 300, 400 with knotless fixation devices such as fixation device 70, and the disclosure contemplates the use of suturing constructs 100, 200, 300, 400 with any type of fixation device, knotless or knotted, or combination of knotless and knotted fixation devices. The exemplary constructs of the present disclosure may be employed in various tissue repairs such as knotless rotator cuff repair with the SpeedBridge™ and SpeedFix™ repair techniques, or similar reattachment techniques of soft tissue to bone employing knotless fixation devices for the formation of single, double or multiple row constructs in arthroscopic rotator cuff repairs, or high demand applications like AC joint reconstruction and other areas where tissue pull-through may be a concern.

Strands 10, 50 may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Strands 10, 50 may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical construct 100, 200, 300, 400 can be used with any type of flexible material or suture known in the art.

The strands may be also formed of a stiff material, or combination of stiff and flexible materials, depending on the intended application. The strands may be also coated and/or provided in different colors. The strands may be also provided with tinted tracing strands, or otherwise contrast visually with the remaining elements of the construct, which could be a plain, solid color, or display a different tracing pattern, for example. Various structural elements of surgical construct 100, 200, 300, 400 may be visually coded, making identification and handling of the suture legs simpler. Easy identification of suture in situ is advantageous in surgical procedures, particularly during arthroscopic surgeries, such as endoscopy and laparoscopy.

Surgical construct 100, 200, 300, 400 may include surgical sutures or similar materials that may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

Preferably, elongated tapered end 25 may have a very fine end that is coated, impregnated, or stiffened with a material such as plastic, for example.

The disclosed suturing constructs have a central strand of core suture with fixed "ratchets" at defined intervals, similar to a bathroom drain chain. Preferably, the ratchets/enlargements are asymmetric with a tapered end towards the cinch. After appropriately defined working distance length, the suture would be the same as a cored #2 FibreWiret, then tapered to a smaller 2.0 FiberWiret to facilitate loading in the cinch mechanism.

Suturing constructs 100, 200, 300, 400 of the present disclosure discussed above may be employed by themselves, as discussed above, and also with various soft and/or hard anchor devices to form suture anchor assemblies 111, 112, 113, 114, 115, 116, 117 detailed below.

For example, FIG. 20 illustrates suture anchor assembly 111 with fixation device or anchor 71 and exemplary suture construct 100 coupled to the anchor body by locking loop 100a. Locking loop 100a is located on top of the anchor 71 but fixed to the anchor body by, for example, static knot 72.

FIG. 21 shows suture anchor assembly 112 that includes fixation device or anchor 71 and exemplary suture construct 100 coupled to the anchor body. Suture construct 100 extends within the body of the anchor 71 and around a post 73 or similar structure located at a distal end of the anchor body. When the bumpy suture 100 is pulled into (by pulling in a tightening direction such as the direction of arrow "A1" (FIG. 21)), the bumpy suture is locked into/inside the anchor body. Anchor 71 may be pre-placed into a bone hole or opening.

FIG. 22 illustrates suture anchor assembly 113 that includes fixation device 75 in the form of a button 75 and exemplary suture construct 100 coupled to the button 75. Button 75 is illustrated with two through openings or apertures 75a that, together with enlargements 55 of the construct 100, could securely lock suturing construct 100; however, the disclosure contemplates any device/button with any shape/configuration (i.e., oval, round, elliptical, S-shaped button, etc.) and with any number of openings/holes that could accommodate at least a part of exemplary construct 100.

Figure 23:
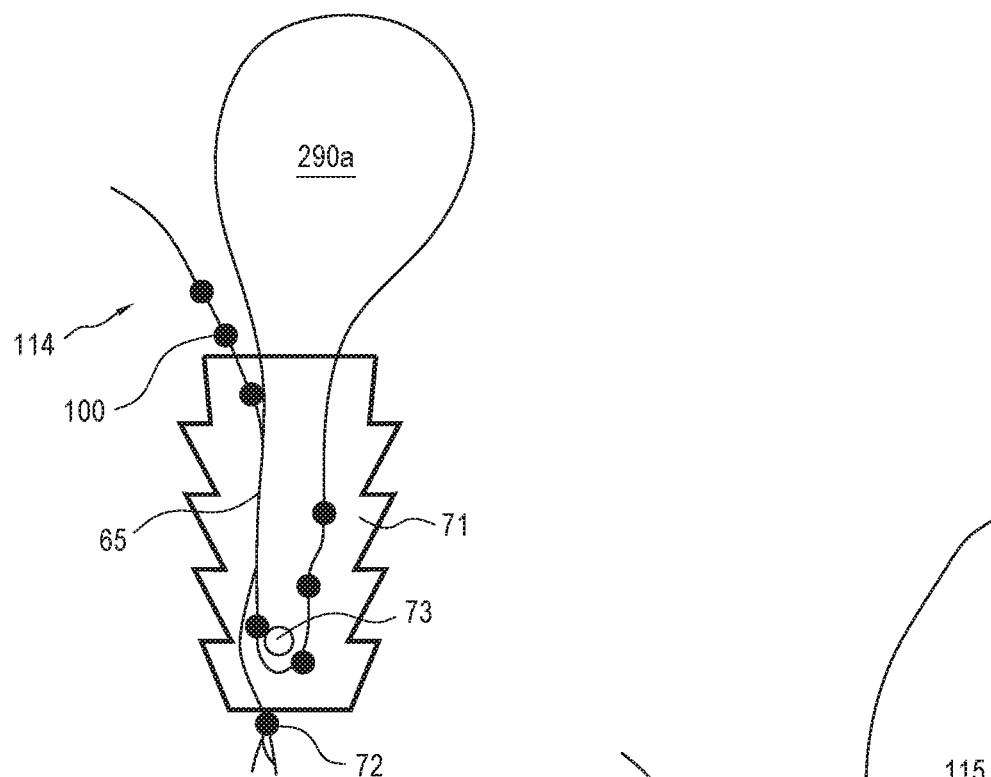
Figure 24:
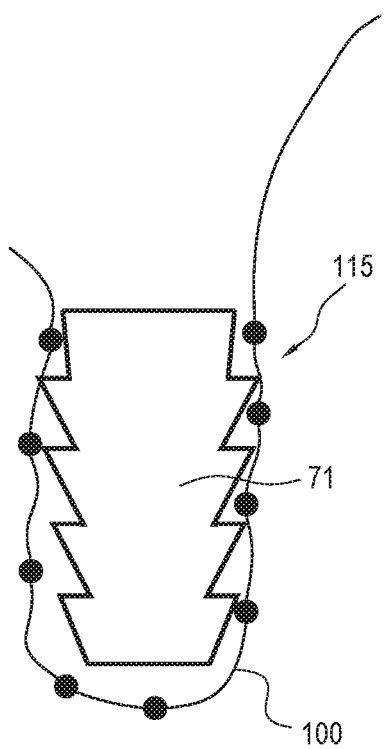

FIG. 23 illustrates exemplary suture construct 100 coupled to a knotless anchor to form exemplary suture anchor assembly 114. Bumpy suture (suture construct) 100 is trapped inside the body of the knotless anchor, as part of the knotless anchor. Suture construct 100 is secured fixedly to the anchor body by static knot 72 and forms a loop 290a and splice 65 within the body of the anchor. The splice may be formed by employing a shuttling device (such as shuttling device 60 with loop 61, discussed above). The loop 290a may is a closed, flexible, knotless, adjustable loop having an adjustable perimeter, and located partially within the body of the anchor 71. The splice 65 may be located wholly within the body of anchor 71. The suture construct 100 may be looped around post 73 (or similar structure) located at a distal end of the knotless anchor body.

Suture anchor assembly 115 (FIG. 24) includes exemplary suture construct 100 located between anchor body 71 and bone, i.e., located on an outer surface of the anchor to provide increased tissue fixation.

Figure 25:
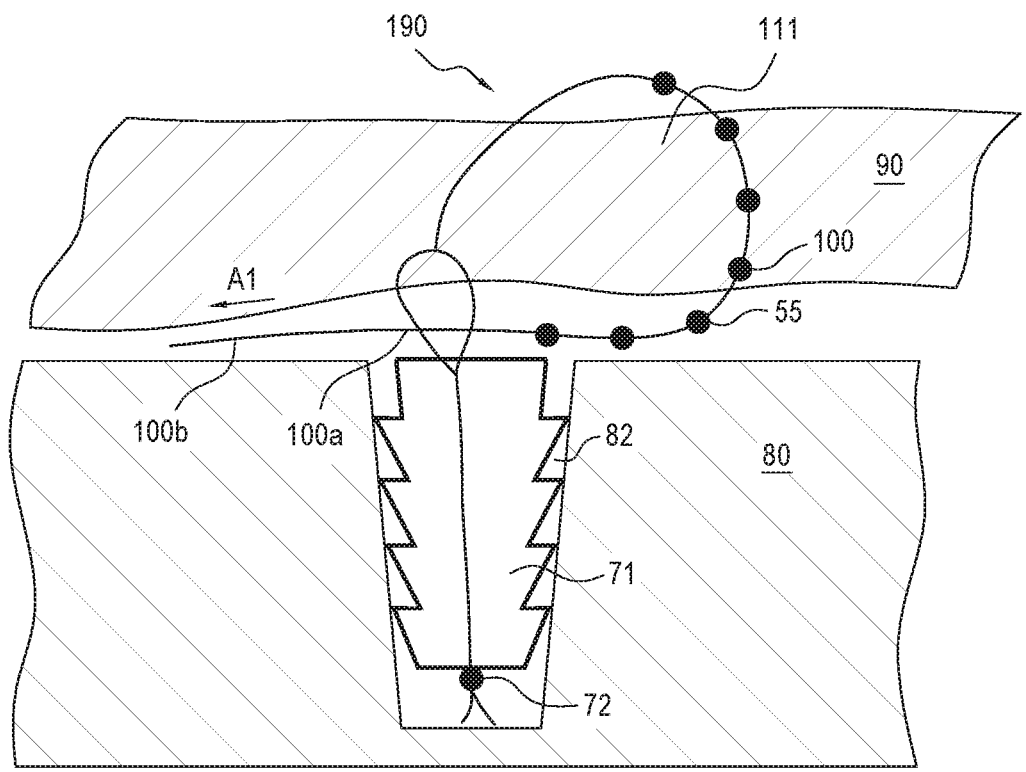
FIG. 25 illustrates the suture anchor assembly of FIG. 20 securing a first tissue to a second tissue.
Figure 26:
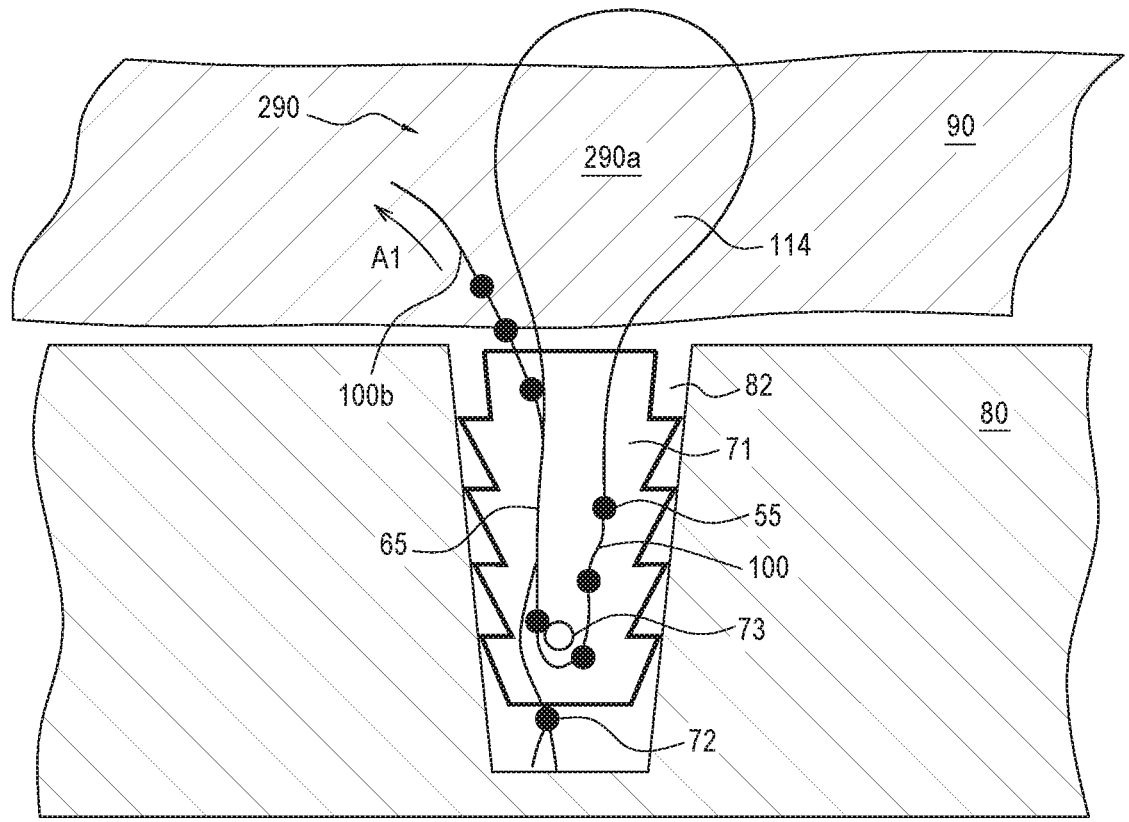
FIG. 26 illustrates the suture anchor assembly of FIG. 23 securing a first tissue to a second tissue.

FIGS. 25 and 26 illustrate exemplary suture anchor assemblies 111 and 114, respectively, employed to attach a first tissue 90 to a second tissue 80, for example, soft tissue 90 to bone 80. Suture anchor assemblies 111, 112, 113, 114, 115 of the present disclosure offer a simplified tissue repair while ensuring positive fixation of first tissue to second tissue.

Exemplary suture anchor assembly 111 formed of anchor 71 pre-loaded with suture construct 100 (bumpy suture 100)

is installed into a pre-drilled hole/socket/opening 82 formed into bone 80. Insertion of anchor 71 into bone preferably forms a tight fit to anchor the suture construct 100 therein. Once the suture anchor assembly 111 is installed into bone hole 82, tissue fixation end 100b of suture construct 100 remains outside of the bone hole 82. Tissue fixation end 100b is passed through soft tissue 90 and loop 100a, and then pulled away from the bone 80 in a tightening direction A1 (FIG. 25) to allow enlargements 55, 155, 255, 355 to lock into place the device and prevent the strand 10/50 of suturing construct 100 from moving in the opposite direction (i.e., in a loosening direction) and form final repair 190.

FIG. 26 illustrates final repair 290 wherein suture anchor assembly 114 is installed into bone hole 82, with tissue fixation end 100b of suture construct 100 remaining outside of the bone hole 82 and forming closed, knotless, flexible, adjustable loop 290a around tissue 90. Closed, knotless, adjustable loop 290a is locked into place by enlargements 55, 155, 255, 355 that prevent the suture end from moving in the opposite direction of A1, i.e., in the direction opposite to the tightening direction A1.

Suturing constructs 100, 200, 300, 400 of the present disclosure discussed above may be employed by themselves, and/or with anchors with hard bodies, as discussed above, and also with soft anchors to form exemplary soft anchor assembly 116 detailed below and with reference to FIG. 27.

Figure 27:
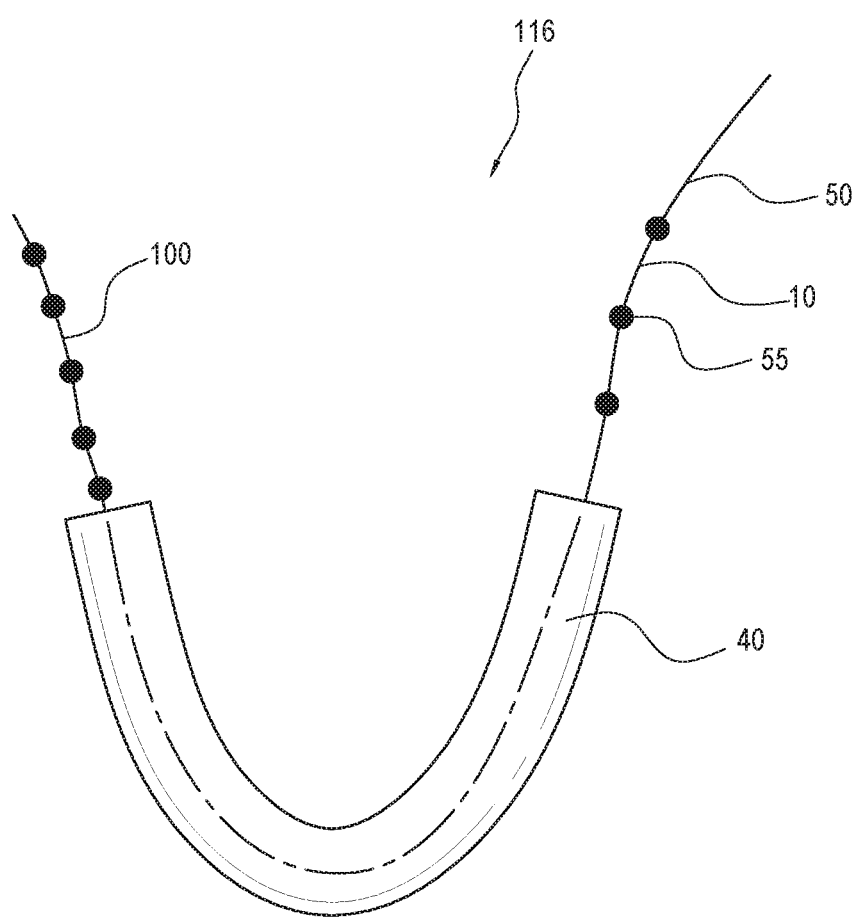
FIG. 27 illustrates an exemplary soft suture anchor assembly.

FIG. 27 illustrates soft suture anchor 40 pre-loaded with suture construct 100. Soft suture anchor 40 is a soft anchor that may include a tubular sheath such as disclosed in U.S. Pat. No. 9,463,011 to Dreyfuss et al., the whole disclosure of which is incorporated by reference in its entirety herein. Tubular sheath 40 may be formed of a flexible material such as suture or polyester or the like, and may be a woven, braided, or knitted structure, and/or may be formed of yarns, fibers, filaments, sutures, braids or similar materials, or combinations thereof. Tubular sheath 40 has two opposing open ends through which suture construct 100 exits. One or both ends of the suture construct 100 may be coupled to various structures such as a shuttling device, another fixation device, a loop, etc., to allow passing of the ends through and/or around soft tissue and securing of the soft tissue to bone.

As detailed in U.S. Pat. No. 9,463,011 to Dreyfuss et al., the tubular sheath which is pre-loaded with the suture construct 100 is inserted and secured into bone, for example, by being inserted and secured into a pre-drilled hole/socket/opening formed into bone, so that the tubular sheath bunches up within the bone hole and, therefore, fixes securely into place into the bone hole. To facilitate the insertion and installation of the tubular sheath 40 into bone, an inserter with a forked tip and/or a mallet tool may be employed.

Once the tubular sheath 40 is inserted into the bone hole, at least one end of the suture construct 100 is passed through/around soft tissue to allow formation of a closed, knotless, flexible, adjustable loop around soft tissue 90 as well as engagement of the enlargements 55, 155, 255, 355 to lock into place the device and prevent the strand 10/50 of construct 100 from moving in the opposite direction (i.e., in a loosening direction). Enlargements 55, 155, 255, 355 may also engage the tubular sheath 40 to lock the final repair into place to secure attachment of soft tissue to bone. The enlarged dimensions of the enlargements 55, 155, 255, 355 relative to the strand 10/50 prevent the final repair from loosening.

FIG. 28 illustrates yet another exemplary suture anchor assembly 117 of the present disclosure. As in the previously-described embodiments, and for simplicity, suture anchor assembly 117 is explained with reference to exemplary construct 100; however, the present disclosure has applicability to any of the constructs 100, 200, 300, 400, in any combination and/or by themselves and/or with other additional fixation devices. As detailed below, exemplary anchor assembly 117 includes one or more bumpy sutures loaded into a pre-placed anchor, tensioned then internally and fixed with a splined insert.

Suture anchor assembly 117 of FIG. 28 includes fixation device or anchor 71a and exemplary suture construct 100 coupled to the anchor body by loop 11a. Loop 11a is located within the body of the anchor 11a and at a distal end of the body of the anchor 71a. Loop 11a may be insert molded within the anchor body and/or may be fixed to the anchor body by, for example, static knot 72a.

Exemplary suture construct 100 is coupled to the anchor body of device 71a. Suture construct 100 extends within the body of the anchor 71a and through the loop 11a located at the distal end of the anchor body. As shown in FIG. 28, bumpy suture 100 is passed through the loop 11a and extends along first and second longitudinal passages 74, 74a located within the anchor body and in communication with each other. Diameter D1 of first passage 74 is greater than diameter D2 of second passage 74a. The first and second passages 74, 74a may extend along longitudinal axis of anchor body of anchor 71, and may be optionally concentrically located relative to each other.

Suture construct 100 of assembly 117 may be optionally and additionally secured with a locking element, for example, an insert 73 provided with a plurality of arms/legs/prongs 73a extending from threaded body 73b. Body 73b of insert 73 is designed to matingly engage a most distal threaded end of driver 76. Insert 73 may be deployable within the anchor body of anchor 71. For example, insert 73 may be provided with deployable or expandable arms/legs/prongs 73a which, in a first position, are in a first undeployed or closed state and, in a second position, are in a second deployed or open state.

In an exemplary-only embodiment, insert 73 is provided with arms/legs/prongs 73a which, in a first position and when inserted through second passage 74a, are in a first state (undeployed or closed) and, in a second position and when inserted into first passage 74, are in a second state (deployed or open). When in the deployed position, arms/legs/prongs 73a are located fully within first passage 74 and exert lateral pressure on longitudinal interior walls of first passage 74 and also on the portion of bumpy suture 100 located within the first passage 74. Body 73b of insert 73 has an outer diameter about equal to diameter D2 of the second passage 74a. When in the deployed state, the most outer diameter of arms/legs/prongs 73a is about equal to diameter D1 of the first passage 74. In this manner, the insert 73 internally fixes and locks the suture construct 100 in place, i.e., the bumpy suture is locked into/inside the anchor body. Enlargements 55, 155, 255, 355 are locked in place by the insert 73 (i.e., locked between the inner walls of the first passage 74 and the arms/legs/prongs 73a of insert 73) and prevent the final repair from loosening. Anchor 71 may be pre-placed into a bone hole or opening. In this exemplary embodiment, the suture construct 100 is fixed and secured/locked to anchor 71 by both loop 11a and insert 73.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A suturing construct, comprising:
   a coreless suture terminating in a first end and in a second end opposite to the first end, wherein the second end is a tapered end portion;
   an inner filament with a plurality of enlargements, wherein the plurality of enlargements form a series of bumps along the inner filament, wherein each of the plurality of enlargements has an outer diameter greater than an outer diameter of the coreless suture so that, when the inner filament with the plurality of enlargements is inserted into the coreless suture, the inner filament and the plurality of enlargements located between the first end and the second end of the coreless suture are all completely covered by the coreless suture and form a bumpy construct; and
   a locking mechanism at the first end, wherein the locking mechanism of the coreless suture is a closed loop.

2. The suturing construct of claim 1, wherein the plurality of enlargements do not penetrate an outer surface of the coreless suture.

3. The suturing construct of claim 1, wherein the plurality of enlargements are barbs, knots, beads, protuberances or combinations thereof.

4. The suturing construct of claim 1, wherein the plurality of enlargements allow locking of the suturing construct.

5. The suturing construct of claim 1, wherein each of the plurality of enlargements has an outer diameter greater than an outer diameter of the inner filament.

6. The suturing construct of claim 1, wherein the coreless suture is a coreless braid or sheath formed of twisted yarns of ultrahigh molecular weight polyethylene that are braided together.

7. The suturing construct of claim 1, wherein the coreless suture is a coreless braid or sheath formed of polyester yarns.

8. The suturing construct of claim 1, wherein the closed loop is formed by splicing the first end through the coreless suture to form a splice and the closed loop.

9. The suturing construct of claim 1, wherein the closed loop is configured to form a racking hitch loop.

10. The suturing construct of claim 1, further comprising a shuttling device attached to the closed loop.

11. The suturing construct of claim 10, wherein the shuttling device is a Nitinol loop.

12. The suturing construct of claim 1, wherein the tapered end portion has three varying widths.

13. The suturing construct of claim 1, further comprising a coating provided over the coreless suture.

14. The suturing construct of claim 13, wherein the coating is a silicon or collagen coating.

15. The suturing construct of claim 1, wherein the coreless suture passes through at least one eyelet of a knotless fixation device.

16. The suturing construct of claim 15, wherein the knotless fixation device is a swivel anchor or a pushlock anchor.

17. The suturing construct of claim 15, wherein the knotless fixation device comprises an anchor body and an anchor tip rotatably attached to the anchor body, and wherein the anchor body is configured to be inserted over the anchor tip for securing the fixation device into bone.

18. The suturing construct of claim 17, wherein the anchor body is a cannulated interference screw.

19. The suturing construct of claim 1, wherein the coreless suture is coupled to an anchor body.

20. The suturing construct of claim 19, wherein the anchor body is soft.

21. The suturing construct of claim 19, wherein the anchor body is rigid.

* * * * *